United States Patent
Ritter

(10) Patent No.: US 9,968,341 B2
(45) Date of Patent: May 15, 2018

(54) DENTAL BITE BLOCK ASSEMBLY

(71) Applicant: ASCENTCARE DENTAL LABS, LLC, Nunica, MI (US)

(72) Inventor: Austin Rasmussen Ritter, Nunica, MI (US)

( * ) Notice: Subject to any disclaimer, the term of this patent is extended or adjusted under 35 U.S.C. 154(b) by 83 days.

(21) Appl. No.: 15/133,555

(22) Filed: Apr. 20, 2016

(65) Prior Publication Data
US 2016/0310234 A1    Oct. 27, 2016

Related U.S. Application Data

(60) Provisional application No. 62/150,448, filed on Apr. 21, 2015.

(51) Int. Cl.
| | | |
|---|---|---|
| *A61C 13/00* | (2006.01) | |
| *A61B 13/00* | (2006.01) | |
| *A61C 17/06* | (2006.01) | |
| *A61C 1/08* | (2006.01) | |
| *A61B 1/24* | (2006.01) | |
| *A61B 1/32* | (2006.01) | |

(Continued)

(52) U.S. Cl.
CPC .......... *A61B 13/00* (2013.01); *A61B 1/24* (2013.01); *A61B 1/32* (2013.01); *A61C 1/088* (2013.01); *A61C 17/043* (2013.01); *A61B 1/06* (2013.01); *A61B 90/16* (2016.02)

(58) Field of Classification Search
CPC . A61C 17/00; A61C 17/0208; A61C 17/0211; A61C 17/043; A61C 17/04; A61C 5/14; A61C 5/90; A61C 5/84; A61B 1/24; A61B 90/16; A61M 16/0493; A61M 16/0488; A61F 5/56; A61F 5/566
USPC ........................................................ 433/93
See application file for complete search history.

(56) References Cited

U.S. PATENT DOCUMENTS

| | | | | |
|---|---|---|---|---|
| RE20,389 E | * | 6/1937 | Pickett ................... | A61B 1/24 254/104 |
| 2,220,674 A | * | 11/1940 | Bloomheart ........... | A61C 5/90 600/238 |

(Continued)

OTHER PUBLICATIONS

LEAP Illuminated Mouth Prop, https://garrisondental.com/en/leap-illuminated-mouth-prop, Garrison Dental, Spring Lake, MI (undated).

(Continued)

*Primary Examiner* — Nicholas Lucchesi
*Assistant Examiner* — Shannel Wright
(74) *Attorney, Agent, or Firm* — James E. Shultz, Jr.

(57) ABSTRACT

A dental bite block assembly includes a U-shaped mounting base having an upper bite portion, a lower bite portion, a central portion, an accessory mount, and a first magnetically energetic material embedded in the central portion of the U-shaped mounting base proximate the accessory mount. A dental accessory has a dental bite block mount that is detachably coupled with the accessory mount of the U-shaped mounting base and a second magnetically energetic material disposed in the dental accessory proximate the dental bite block mount. When the dental bite block mount is coupled with the accessory mount, the first magnetically energetic material embedded in the central portion of the U-shaped mounting base and the second magnetically energetic material disposed in the dental accessory are in operable magnetic engagement with each other.

4 Claims, 21 Drawing Sheets

(51) Int. Cl.
*A61B 1/06* (2006.01)
*A61B 90/16* (2016.01)

(56) References Cited

U.S. PATENT DOCUMENTS

| | | | |
|---|---|---|---|
| 2,823,455 A | 4/1956 | Sprague | |
| 3,657,819 A | 4/1972 | Soderqvist | |
| 3,722,101 A | 3/1973 | Via, Jr. | |
| 3,916,880 A | 11/1975 | Schroer | |
| 3,924,333 A | 12/1975 | Erickson | |
| 4,017,975 A | 4/1977 | Johnson | |
| 4,024,859 A | 5/1977 | Slepyan et al. | |
| 4,112,936 A | 9/1978 | Blachly | |
| 4,167,814 A * | 9/1979 | Schubert | A61C 17/043 433/93 |
| 4,215,984 A | 8/1980 | Reichley | |
| 4,310,308 A | 1/1982 | Oien | |
| 4,425,911 A | 1/1984 | Luomanen et al. | |
| 4,495,954 A | 1/1985 | Liegner | |
| D292,123 S | 9/1987 | Armstrong et al. | |
| 4,802,851 A * | 2/1989 | Rhoades | A61C 17/043 433/140 |
| 4,975,057 A * | 12/1990 | Dyfvermark | A61B 1/24 433/91 |
| 5,071,347 A | 12/1991 | McGuire | |
| 5,078,602 A | 1/1992 | Honoshofsky | |
| 5,097,820 A | 3/1992 | Shulman et al. | |
| 5,347,996 A * | 9/1994 | Huan | A61B 1/24 128/859 |
| 5,386,821 A | 2/1995 | Poterack | |
| 5,421,327 A | 6/1995 | Flynn et al. | |
| D370,732 S | 6/1996 | Smith | |
| 5,590,643 A | 1/1997 | Flam | |
| 5,733,121 A | 3/1998 | Goode | |
| 5,740,791 A | 4/1998 | Aves | |
| 5,762,496 A | 6/1998 | Albertsson et al. | |
| 5,827,061 A * | 10/1998 | Goodman | A61C 17/043 433/93 |
| 6,098,627 A | 8/2000 | Kellner et al. | |
| 6,102,701 A | 8/2000 | Engeron | |
| D440,654 S | 4/2001 | Mark | |
| D441,073 S | 4/2001 | Mark | |
| 6,241,521 B1 * | 6/2001 | Garrison | A61B 1/24 433/140 |
| 6,474,332 B2 | 11/2002 | Arndt | |
| 6,652,276 B2 | 11/2003 | Fischer et al. | |
| 6,655,960 B2 | 12/2003 | Fischer | |
| 6,675,808 B2 | 1/2004 | Karasic | |
| 6,716,029 B2 | 4/2004 | Fischer et al. | |
| D495,799 S | 9/2004 | Hirsch et al. | |
| 7,066,735 B1 * | 6/2006 | Gasporra | A61C 5/90 433/140 |
| 7,712,468 B2 | 5/2010 | Hargadon | |
| 7,780,445 B2 | 8/2010 | Keles | |
| 7,785,105 B2 | 8/2010 | Anderson | |
| 7,887,483 B2 | 2/2011 | Rosenberg | |
| D639,959 S | 6/2011 | Westerlund | |
| 8,029,280 B2 * | 10/2011 | Black | A61C 17/043 433/140 |
| 8,083,672 B2 | 12/2011 | Minson | |
| 8,197,402 B1 | 6/2012 | Cedeno | |
| D666,726 S | 9/2012 | Davis et al. | |
| 8,430,095 B2 | 4/2013 | Inoue et al. | |
| 8,535,056 B2 | 9/2013 | Dragan et al. | |
| 8,656,925 B2 | 2/2014 | Davis et al. | |
| 8,684,919 B2 | 4/2014 | Anca et al. | |
| 8,770,189 B2 | 7/2014 | Colman et al. | |
| 8,820,320 B2 | 9/2014 | Filipi et al. | |
| 8,870,568 B1 * | 10/2014 | Ream | A61C 17/043 433/93 |
| D721,811 S | 1/2015 | Zakhem et al. | |
| D753,818 S | 4/2016 | Maguire et al. | |
| D762,856 S | 8/2016 | Steward, Jr. | |
| 2001/0015206 A1 | 8/2001 | Arndt | |
| 2001/0039949 A1 | 11/2001 | Loubser | |
| 2005/0103331 A1 * | 5/2005 | Wedemeyer | A61F 5/566 128/200.24 |
| 2005/0239018 A1 * | 10/2005 | Green | A61C 5/90 433/140 |
| 2006/0042637 A1 | 3/2006 | Martin et al. | |
| 2006/0110705 A1 * | 5/2006 | Jensen | A61C 5/90 433/140 |
| 2007/0068535 A1 | 3/2007 | Colman et al. | |
| 2007/0148619 A1 * | 6/2007 | Anderson | A61C 17/043 433/136 |
| 2008/0053434 A1 | 3/2008 | Wightman et al. | |
| 2008/0156322 A1 * | 7/2008 | Isenberg | A61M 16/0488 128/200.26 |
| 2008/0202529 A1 * | 8/2008 | Flory | A61M 16/0488 128/207.17 |
| 2008/0318183 A1 * | 12/2008 | Suzman | A61C 17/04 433/93 |
| 2009/0274991 A1 * | 11/2009 | Black | A61C 17/043 433/93 |
| 2010/0129767 A1 | 5/2010 | Fishburne, Jr. | |
| 2010/0132700 A1 | 6/2010 | Filipi et al. | |
| 2010/0262033 A1 | 10/2010 | Colman et al. | |
| 2010/0317987 A1 | 12/2010 | Inoue et al. | |
| 2011/0229847 A1 * | 9/2011 | Worthington | A61C 17/043 433/93 |
| 2011/0244417 A1 * | 10/2011 | Hilsen | A61C 1/082 433/75 |
| 2011/0251467 A1 | 10/2011 | Poch Marti | |
| 2012/0015320 A1 * | 1/2012 | Koo | A61B 1/24 433/29 |
| 2012/0228528 A1 | 9/2012 | Koo | |
| 2013/0104912 A1 | 5/2013 | Davis et al. | |
| 2013/0245367 A1 | 9/2013 | Tucker | |
| 2013/0270878 A1 | 10/2013 | Adachi et al. | |
| 2013/0323670 A1 | 12/2013 | Okuda et al. | |
| 2014/0007868 A1 | 1/2014 | Eaton et al. | |
| 2014/0114132 A1 | 4/2014 | DeDomenico | |
| 2014/0275803 A1 | 9/2014 | Cushner et al. | |
| 2014/0332009 A1 | 11/2014 | Haider et al. | |
| 2014/0356802 A1 * | 12/2014 | Balog | A61B 1/24 433/29 |
| 2015/0013672 A1 | 1/2015 | Abdoue | |
| 2015/0157821 A1 | 6/2015 | Manecke et al. | |
| 2016/0242885 A1 | 8/2016 | Dickie et al. | |
| 2016/0270878 A1 | 9/2016 | Fulton, III | |
| 2017/0079756 A1 * | 3/2017 | Velky | A61C 17/043 |

OTHER PUBLICATIONS

Olight SR52 Intimidator CREE XM-L2 LED Flashlight, https://www.amazon.com/Oling-Intimidator-XM-L-2-Flashlight-Black/dp/B00KLMDM4S . . . (Jun. 29, 2016).

Garrison Dental, LEAP Illuminated Mouth Prop, https://garrisondental.com/en/leap-illuminated-mouth-prop, Garrison Dental, Spring Lake, MI (undated, but was first published Jan. 11, 2016, and last updated Feb. 9, 2016).

Olight, Olight SR52 Intimidator CREE XM-L2 LED Flashlight, https://www.amazon.com/Oling-Intimidator-XM-L-2-Flashlight-Black/dp/B00KLMDM4S . . . (Jun. 29, 2016).

* cited by examiner

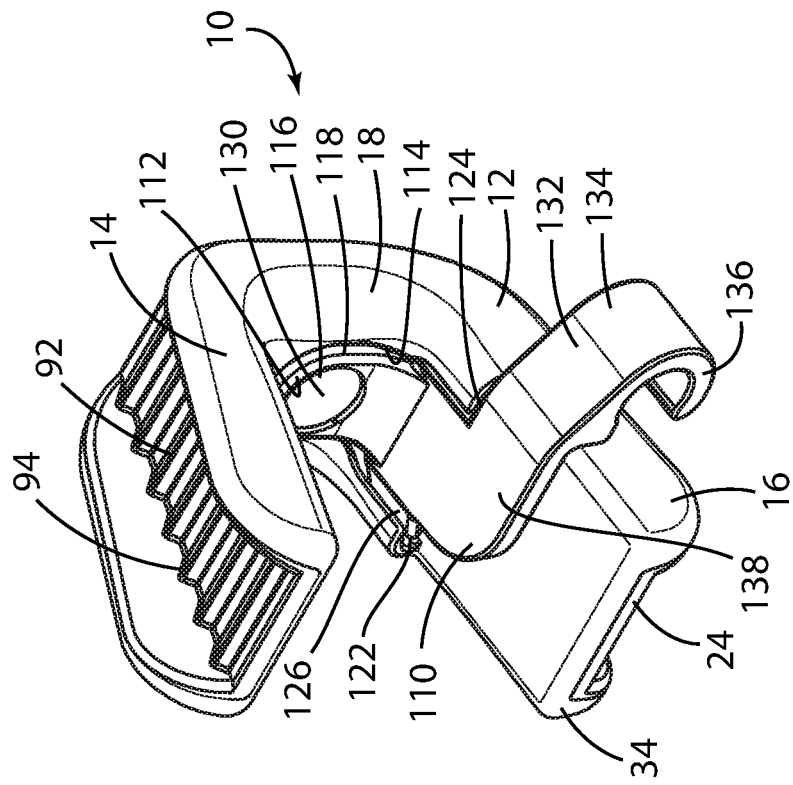
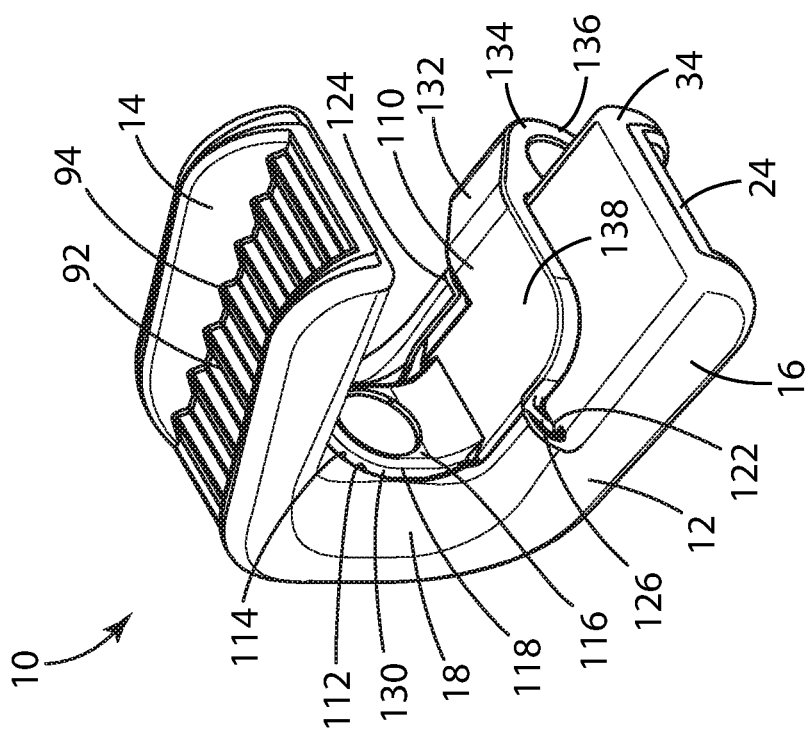
FIG. 8
FIG. 7

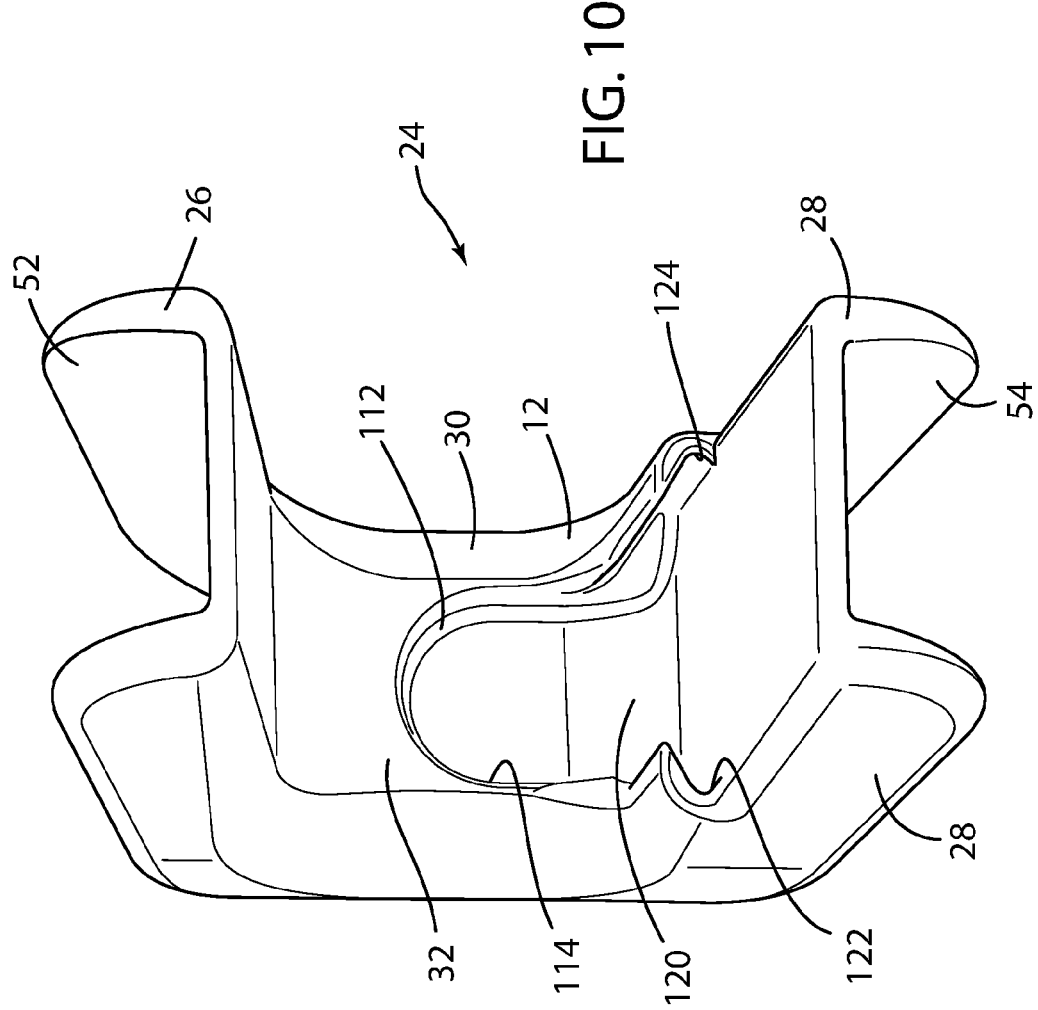

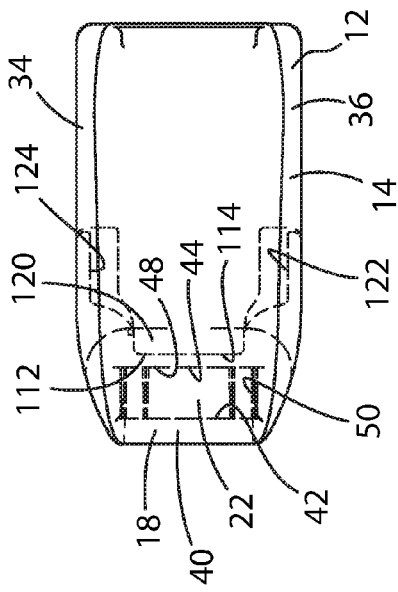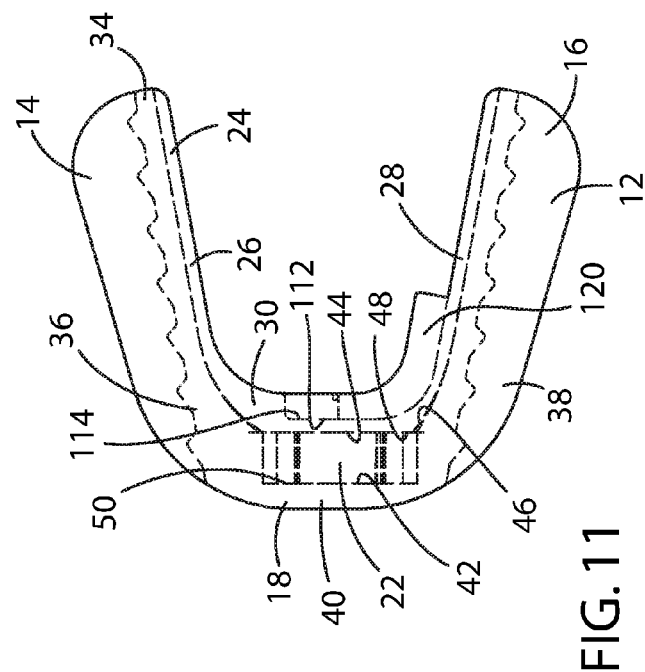

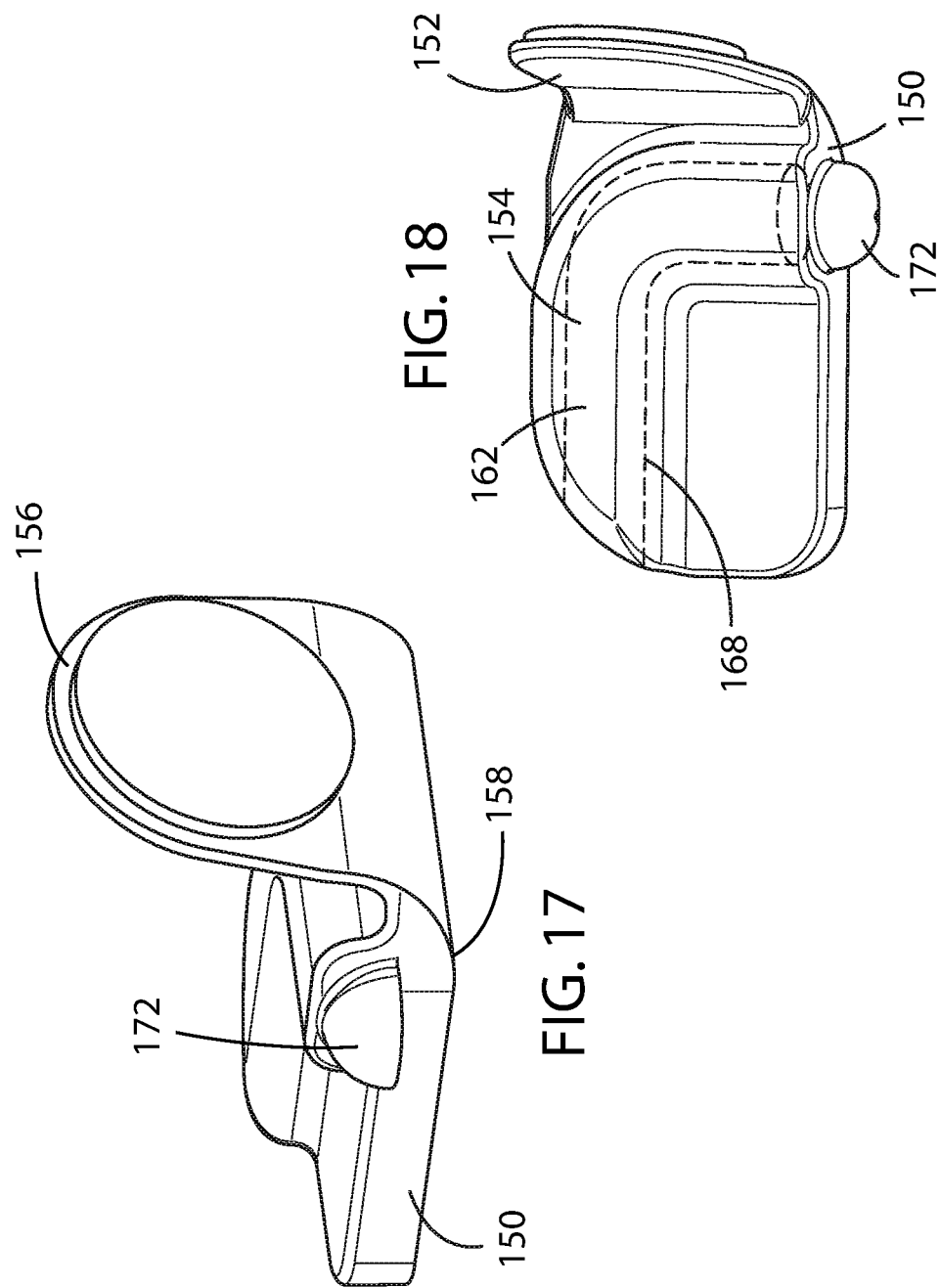

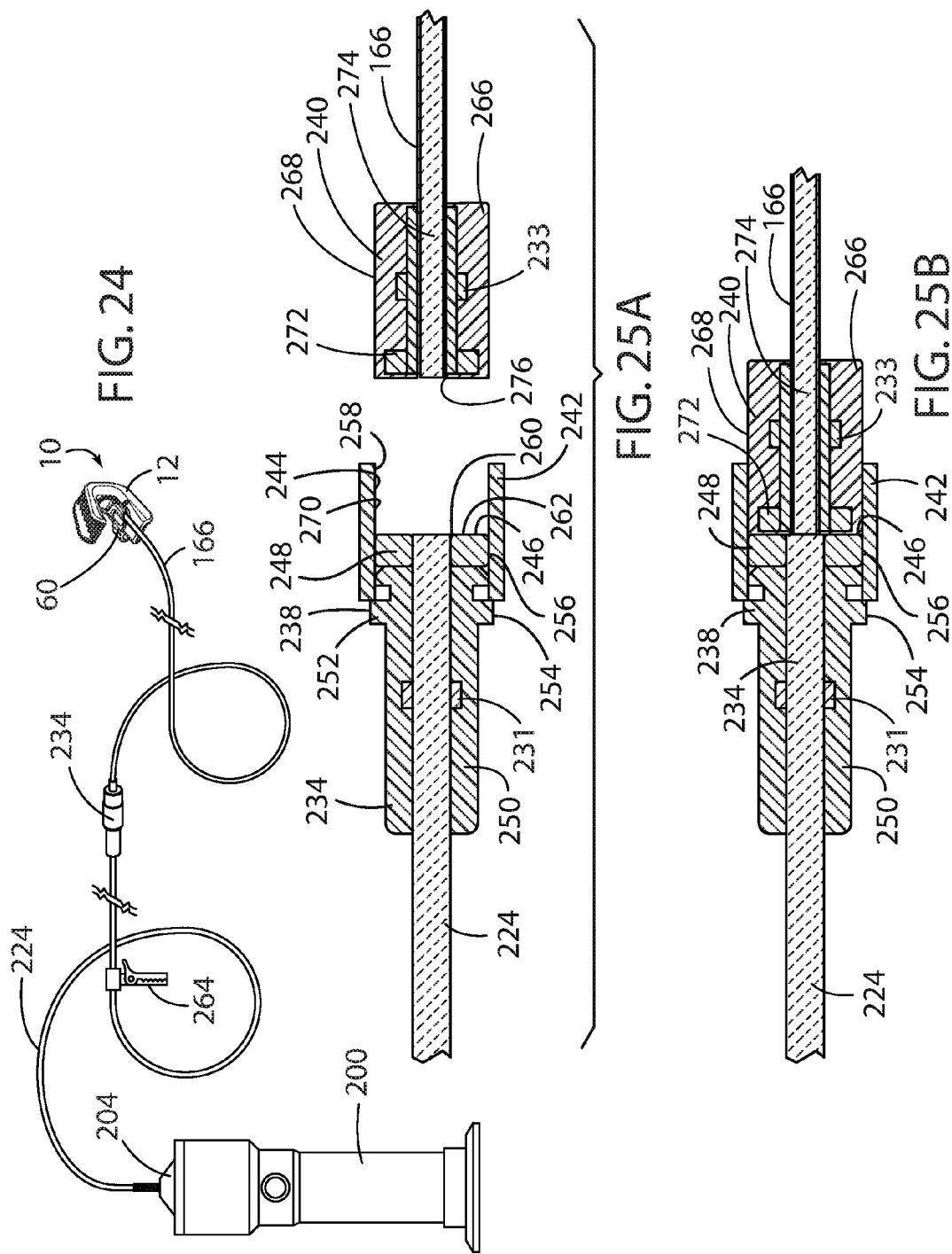

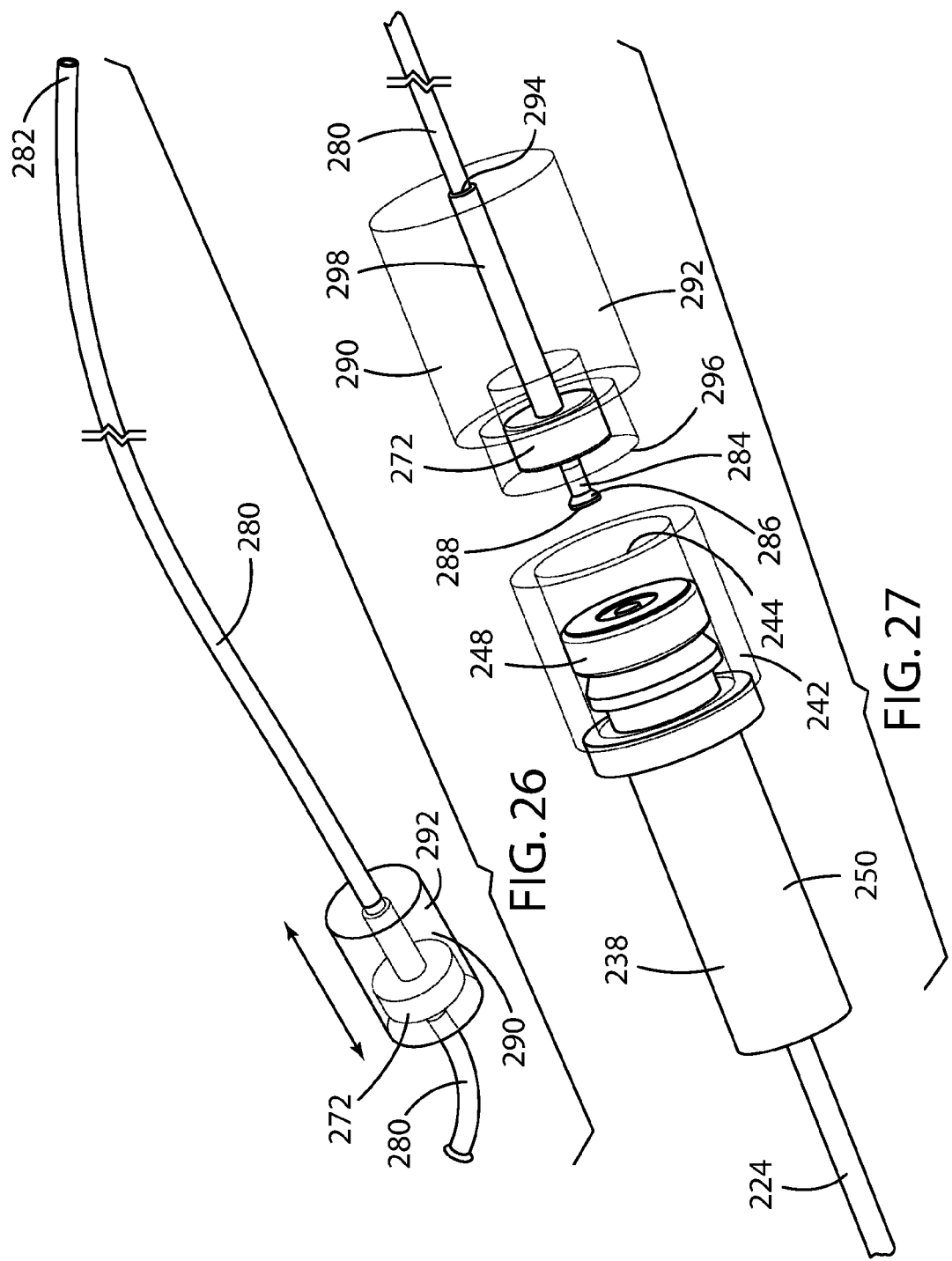

DENTAL BITE BLOCK ASSEMBLY

CROSS-REFERENCE TO RELATED APPLICATION AND CLAIM TO PRIORITY

The present application claims priority under 35 U.S.C. § 119(e) of U.S. Provisional Application 62/150,448, filed Apr. 21, 2015, the entire disclosure of which is incorporated herein by reference.

FIELD OF THE INVENTION

The present invention generally relates to a dental treatment device, and more particularly, to a dental bite block assembly that is adapted to accept and interact with dental treatment accessories.

BACKGROUND OF THE INVENTION

Dental procedures often require a dentist and/or dental hygienist to work under numerous limitations, primarily among them being restricted physical access available for performing dental procedures within a patient's mouth and limited ambient light. For example, during dental procedures that employ high speed drills, the patient's mouth must receive the dental drill unit and a saliva ejection tube to evacuate particulates and/or saliva from the patient's mouth during the dental procedure, which typically requires the assistance of a another person, such as a dental assistant. In addition, again especially during dental procedures that employ high speed drills, the patient's tongue is at risk of injury if left unrestrained, which may also require the assistance of a dental assistant. Thus, the use of dental accessories, such as light sources, saliva ejection tube holders, and tongue suppressors, is occasionally required.

Further, dental procedures can also be lengthy. A patient's masseter, temporalis, medial pterygoid and lateral pterygoid muscles can become tired or sore when the patient's mouth has been open for long periods of time. Prior attempts to alleviate the fatigue that patients experience during dental procedures, however, tend to aggregate the limitations noted above and to further obstruct physical access to the interior of the mouth, interfering with the ability of the dentist or dental hygienist to perform certain dental procedures and limiting light. Further, some prior attempts to relieve fatigue were designed solely for the left or right side of the mouth, limiting their usefulness. In those devices that held a dental accessory, such as a saliva ejection tube, the dental accessary was also difficult to install and required the use of both hands or the complete removal of the device from the patient's mouth to attach and remove the dental accessory. In the case of saliva ejection tubes, such devices were further designed to hold but one type or size of saliva ejection tube and lacked the ability or hold different sized saliva ejection tubes. In addition, sterilization and reuse was problematic because of cracks and crevices in many prior designs.

Prior attempts to alleviate fatigue usually added further obstruction, limiting access for the performance of dental procedures and typically required the use of two hands or a dental assistant to attach or remove a dental accessary, such as a light source, saliva ejection tube holder, and/or tongue suppressor. Hence, a dental bite block assembly which overcomes these drawbacks would be advantageous.

SUMMARY OF THE INVENTION

According to one aspect of the present invention, a dental bite block assembly includes a U-shaped mounting base having an upper bite portion, a lower bite portion, a central portion, an accessory mount, and a first magnetically energetic material embedded in the central portion of the U-shaped mounting base proximate the accessory mount. A dental accessory has a dental bite block mount that is detachably coupled with the accessory mount of the U-shaped mounting base and a second magnetically energetic material disposed in the dental accessory proximate the dental bite block mount. When the dental bite block mount is coupled with the accessory mount, the first magnetically energetic material embedded in the central portion of the U-shaped mounting base and the second magnetically energetic material disposed in the dental accessory are in operable magnetic engagement with each other.

According to another aspect of the present invention, a dental bite block assembly includes a U-shaped mounting base having an upper bite portion, a lower bite portion, a central portion, an accessory mount, a first magnetically energetic material embedded in the central portion of the U-shaped mounting base proximate the accessory mount, and a circular recess concentrically disposed proximate the first magnetically energetic material. A dental accessory fabricated of a stainless steel metal wire fabricated of a second magnetically energetic material that defines the dental bite block mount is detachably coupled with the accessory mount of the U-shaped mounting base. With the dental bite block mount coupled with the accessory mount, the first magnetically energetic material embedded in the central portion of the U-shaped mounting base and the second magnetically energetic material disposed in the dental accessory are in operable magnetic engagement with each other.

According to yet another aspect of the present invention, a dental bite block assembly includes a U-shaped mounting base having an upper bite portion, a lower bite portion, a central portion, an accessory mount disposed on the central portion of the U-shaped mounting base and comprises a forwardly facing recess, and a first magnetically energetic material embedded in the central portion of the U-shaped mounting base proximate the accessory mount. A dental accessory having a dental bite block mount detachably is coupled with the accessory mount of the U-shaped mounting base and a second magnetically energetic material is disposed in the dental accessory proximate the dental bite block mount. The dental bite block mount of the dental accessory comprises a rearwardly facing member within which the second magnetically energetic material is disposed. With the dental bite block mount coupled with the accessory mount, the first magnetically energetic material embedded in the central portion of the U-shaped mounting base and the second magnetically energetic material disposed in the dental accessory are in operable magnetic engagement with each other, and the rearwardly facing member is fittingly received within the recess of the central portion of the U-shaped mounting base.

These and other aspects, objects, and features of the present invention will be understood and appreciated by those skilled in the art upon studying the following specification, claims, and appended drawings.

BRIEF DESCRIPTION OF THE DRAWINGS

In the drawings:

FIG. 7 is a front right perspective view of another embodiment of a dental bite block assembly of the present disclosure;

FIG. 8 is a front left perspective view of the dental bite block assembly of FIG. 7;

FIG. 10 is a front perspective view of the inner bite block member of the U-shaped mounting base of the dental bite block assembly of FIG. 7;

FIG. 11 is a side plan view of the U-shaped mounting base of the dental bite block assembly of FIG. 7;

FIG. 12 is a top plan view of the U-shaped mounting base of the dental bite block assembly of FIG. 7;

FIG. 13 is a front plan view of the U-shaped mounting base of the dental bite block assembly of FIG. 7;

FIG. 17 is a rear perspective view of the light mount of the illuminated dental accessory of FIG. 14;

FIG. 18 is a top perspective view of the light mount of the illuminated dental accessory of FIG. 14;

FIG. 24 is a schematic view of the light delivery system for the dental bite block assembly of the present disclosure;

FIG. 25A is a partial cross-sectional view of the coupled magnetic light coupler of the light delivery system for the dental bite block assembly of FIG. 24;

FIG. 25B is a cross-sectional view of the uncoupled magnetic light coupler of the light delivery system for the dental bite block assembly of FIG. 24;

FIG. 26 is a schematic view of the inspection filament and the inspection filament coupler of the light delivery system for the dental bite block assembly of FIG. 23;

FIG. 27 is a perspective view of the disconnected inspection filament coupler of the light delivery system for the dental bite block assembly of FIG. 26;

DETAILED DESCRIPTION OF THE EMBODIMENTS

Figure 1:
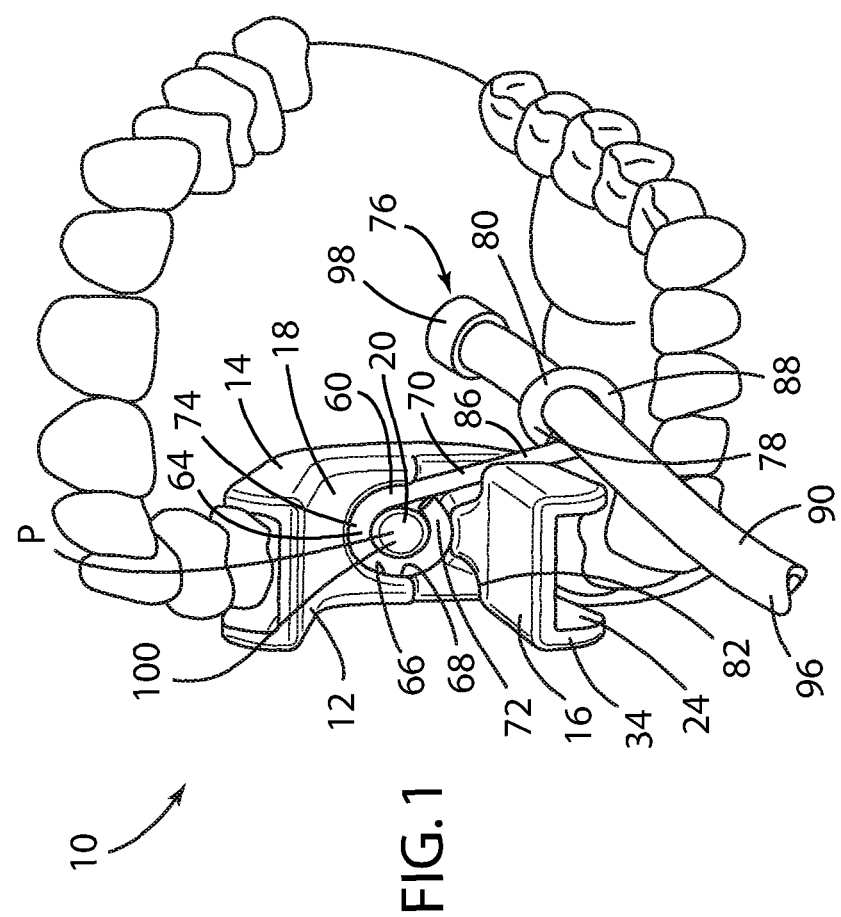
FIG. 1 is a front perspective view of one embodiment of a dental bite block assembly of the present disclosure.

As referenced in the figures, the same reference numerals may be used herein to refer to the same parameters and components or their similar modifications and alternatives. For purposes of description herein, the terms "upper," "lower," "right," "left," "rear," "front," "vertical," "horizontal," and derivatives thereof shall relate to the invention as oriented in FIG. 1. However, it is to be understood that the invention may assume various alternative orientations, except where expressly specified to the contrary. It is also to be understood that the specific devices and processes illustrated in the attached drawings, and described in the following specification are simply exemplary embodiments of the inventive concepts defined in the appended claims. Hence, specific dimensions and other physical characteristics relating to the embodiments disclosed herein are not to be considered as limiting, unless the claims expressly state otherwise. The drawings referenced herein are schematic and associated views thereof are not necessarily drawn to scale.

Figure 2:
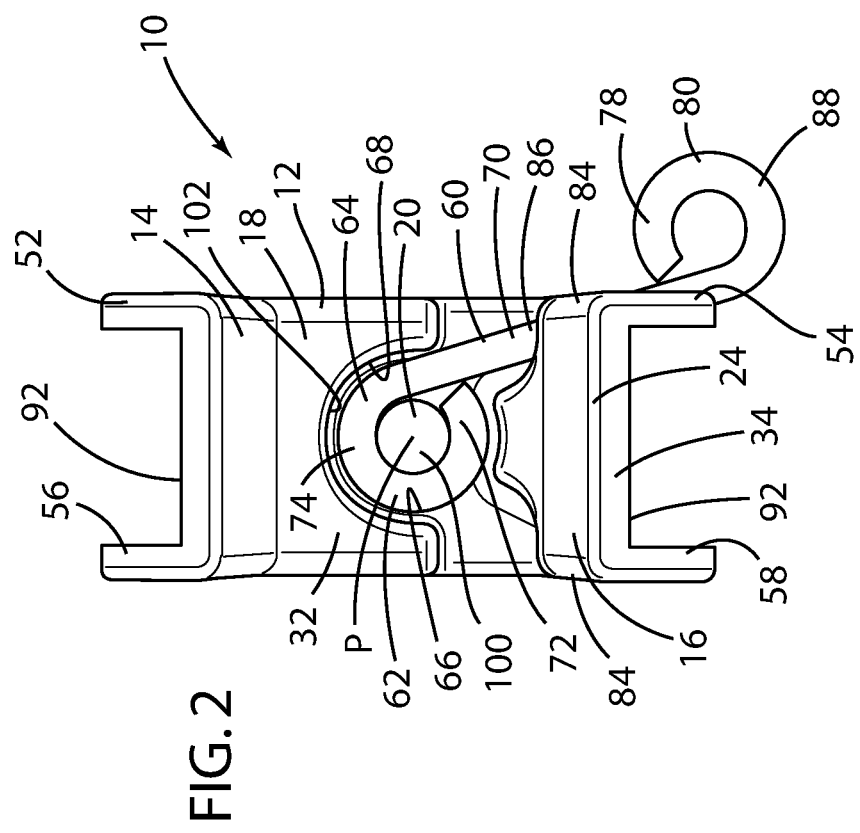
FIG. 2 is a front plan view of the dental bite block assembly of FIG. 1.

Referring to FIGS. 1 and 2, reference numeral 10 generally designates a dental bite block assembly that includes a U-shaped mounting base 12. The U-shaped mounting base 12 has an upper bite portion 14, a lower bite portion 16, a central portion 18, an accessory mount 20, and a first magnetically energetic material 22 embedded in the central portion 18 of the U-shaped mounting base 12 proximate the accessory mount 20.

The U-shaped mounting base 12 comprises an inner bite block member 24 also having a substantially U-shaped configuration and having an upper bite portion 26, a lower bite portion 28, and a central portion 30. The central portion 30 has an exterior surface 32 whereon the accessory mount 20 is disposed. The inner bite block member 24 of the U-shaped mounting base 12 is preferably constructed from latex-free material and is preferably comprised of polypropylene formed via a first injection molding process.

An outer bite block member 34 of the U-shaped mounting base 12 likewise has a substantially U-shaped configuration and likewise has an upper bite portion 36 disposed in juxtaposed relation with the upper bite portion 26 of the inner bite block member 24, a lower bite portion 38 disposed in juxtaposed relation with the lower bite portion 28 of the inner bite block member 24, and a central portion 40 in juxtaposed relation with the central portion 30 of the inner bite block member 24. The outer bite block member 34 is preferably constructed from santoprene thermoplastic vulcanizates (TPV) via a second injection molding process. Preferably, during the second injection molding process, the inner bite block member 24 is used as a part of the mold. Thus, the outer bite block member 34 is caused to bind securely to the polypropylene of the inner bite block member 24 following the second injection process without the need to utilize adhesives and seals. Further, this process allows the creation of a structure that provides protection for the first magnetically energetic material 22 mounted in the U-shaped mounting base 12, as discussed below.

The central portions 18, 30 of each of the inner bite block member 24 and the outer bite block member 34 cooperate to form a cavity 42 proximate the accessory mount 20, within which the first magnetically energetic material 22 is received. The central portion 18 of the inner bite block member 24 has a rearward facing surface 44 and the central portion of the outer bite block member 34 has a forward facing surface 46, and the cavity 42 comprises a first circular recess 48 that forms a circular wall on one of either the rearward facing surface 44 of the inner bite block member 24 or the forward facing surface 46 of the outer bite block member 34. The first magnetically energetic material 22 is received and sealingly encased within the cavity 42 within the U-shaped mounting base 12 during the second injection molding process. Even more preferably, the rearward facing surface 44 of the inner bite block member 24 is provided with the first circular recess 48, and the forward facing surface 46 of the outer bite block member 34 is provided with a corresponding and interlocking second substantially circular recess 50, wherein the first circular recess 48 is received within the second substantially circular recess 50. The first magnetically energetic material 22 is received in the cavity 42 formed by the first circular recess 48 in the second substantially circular recess 50 and is sealingly encased within the cavity 42 within the U-shaped mounting base 12 during the second injection molding process.

The U-shaped mounting base 12 further comprises a pair of flanges 52 extending upwardly from the upper bite portion 26 of the inner bite block member 24 and a pair of flanges 54 extending downwardly from the lower bite portion 28 of the inner bite block member 24. The outer bite block member 34 similarly comprises a pair of flanges 56 extending upwardly from the upper bite portion 36 of the outer bite block member 34 and a pair of flanges 58 extending downwardly from the lower bite portion 38 of the inner bite block member 24. The upwardly extending flanges 56 of the upper bite portion 36 of the outer bite block member 34 are fittingly received within the pair of flanges 52 extending upwardly from the upper bite portion 26 of the inner bite block member 24 and downwardly extending flanges 58 the lower bite portion 38 of the outer bite block member 34 are fittingly received within the pair of flanges 54 extending downwardly from the lower bite portion 28 of the inner bite block member 24.

It should be noted that the U-shaped mounting base 12 can be provided in a number of different sizes, all sharing essentially the same relative proportions and geometry, except for the shape and size of accessory mount 20, such as a torus 68, discussed further below, which should remain the same from size to size in order to properly and fittingly receive the curved portion 74 of the distal and 72 of the dental accessory 60. That is, for larger patients, a large size may be most appropriate. For smaller patients and for children, a smaller pediatric size might be the most appropriate. For those patients of medium or moderate build, a medium or various intermediate sizes may be provided to provide the greatest comfort for any particular patient.

The dental bite block assembly 10 also includes a dental accessory 60 provided with a dental bite block mount 62 that may be detachably coupled with the accessory mount 20 of the U-shaped mounting base 12. A second magnetically energetic material 64 is disposed in or comprises the dental accessory 60 proximate the dental bite block mount 62. With the dental bite block mount 62 coupled with the accessory mount 20, the first magnetically energetic material 22 embedded in the central portion 18 of the U-shaped mounting base 12 and the second magnetically energetic material 64 disposed in or comprising the dental accessory 60 are in operable magnetic engagement with each other.

Preferably, the first magnetically energetic material 22 embedded in the central portion 18 of the U-shaped mounting base 12 is a permanent magnet or a ferromagnetic material and the second magnetically energetic material 64 disposed in or comprising the dental accessory 60 is the other of a permanent magnet or a ferromagnetic material. In accordance with the present disclosure, the permanent magnet is preferably comprised of a neodymium (NdFeB) high curie temperature (Tc) magnetic material, which is preferred due to its ability to maintain its magnetic properties in the environment of the presently disclosed dental bite block assembly 10. This is particularly important in the context of dental tools, such as those described herein, wherein the tools are subject to repeated autoclaving at temperatures exceeding 180° F. for extended periods of time in order to sterilize the dental tools for subsequent use. Thus, a permanent magnetic material that was susceptible to reduction of its magnetic properties at high temperatures would be undesirable.

The neodymium magnet is preferably formed from an axially magnetized sintered neodymium. However, this material tends to be vulnerable to corrosion, especially along grain boundaries of the sintered magnet. As this type of corrosion can cause serious deterioration, including crumbling of a magnet into a powder of small magnetic particles or spalling of a surface layer, the neodymium permanent magnet is preferably encapsulated in a cavity 42 formed by the cooperation of the inner bite block member 24 and the outer bite block member 34, as described above.

With the neodymium high curie temperature magnet as the first magnetically energetic material 22 safely embedded within the U-shaped mounting base 12 and situated proximate to the accessory mount 20, it can be used in combination with the dental accessory 60 containing or constructed of a ferromagnetic material, such as steel, to conveniently position and insecurely hold accessory dental instruments within a patients mouth, as disclosed herein.

In a first embodiment of the dental accessory 60 in accordance with the present disclosure, the accessory mount 20 includes a circular recess 66 preferably formed in the shape of the torus 68 concentrically disposed proximate the first magnetically energetic material 22. In this embodiment, the dental accessory 60 is fabricated of a steel metal wire 70 as the second magnetically energetic material 64. The steel wire 70, comprising a ferromagnetic material, has a first distal end 72 having a curved portion 74 for receiving a dental tool 76 and a second distal end 78 having a curved portion 80 that forms the dental bite block mount 62 and which is fittingly received within the torus 68 disposed upon the exterior surface 32 of the central portion 18 of the U-shaped mounting base 12. Preferably, the outer diameter of the curved portion 80 of the second distal end 78 of the dental accessory 60 is only marginally smaller than the inner diameter of the torus 68, thereby providing a snug and secure fit therebetween.

Figure 4:
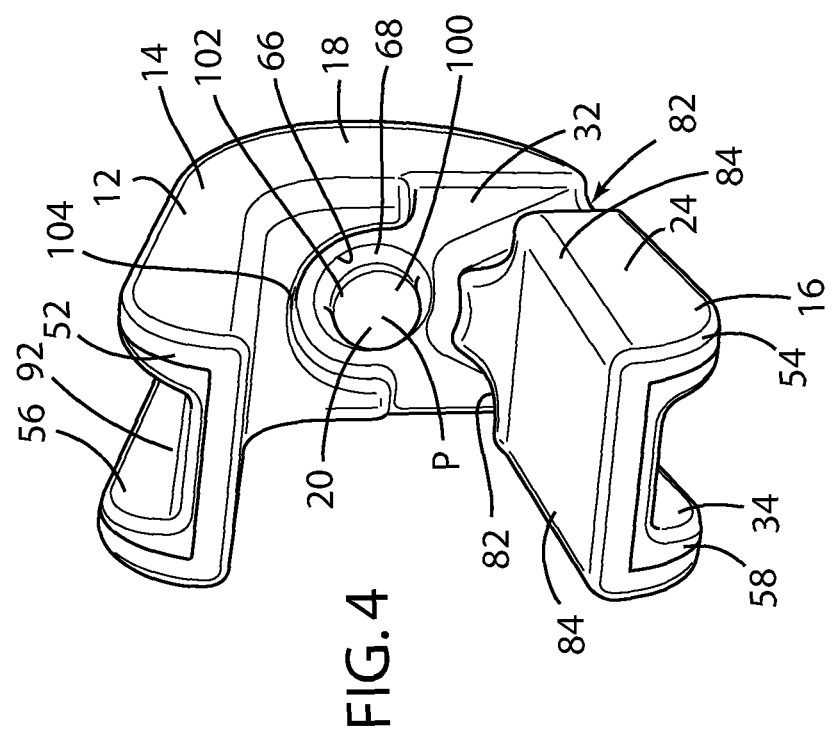
FIG. 4 is a front perspective view of the U-shaped mounting base of the dental bite block assembly of FIG. 1.
Figure 5:
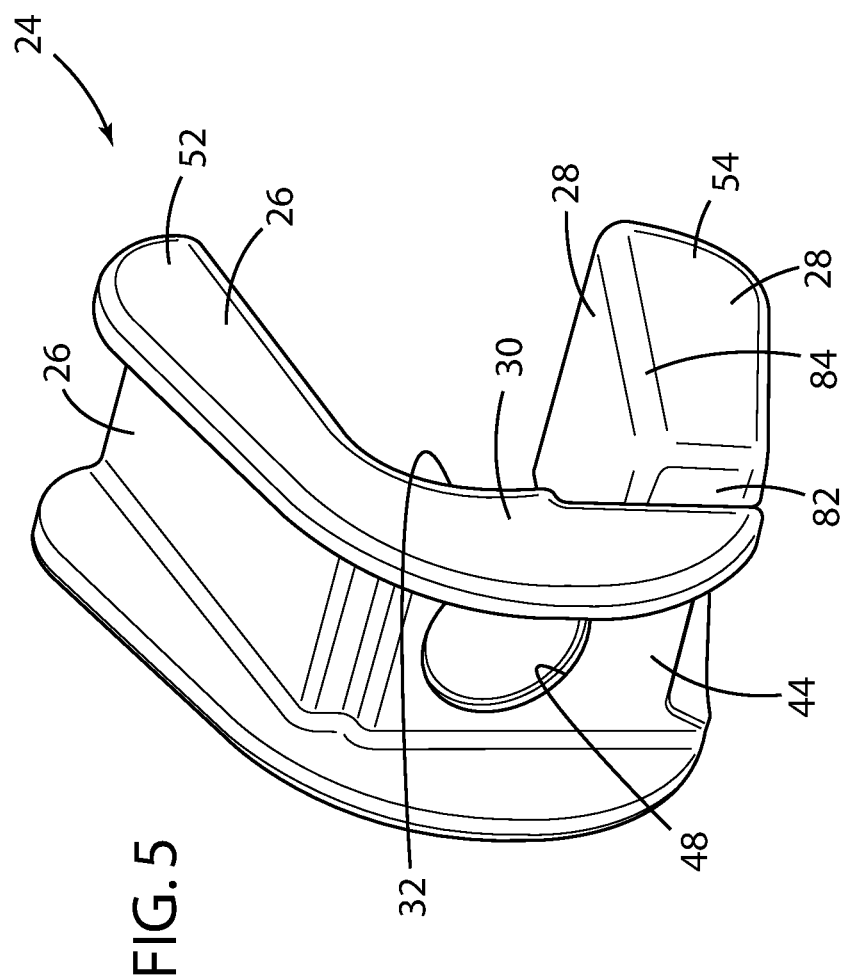
FIG. 5 is a rear perspective view of the inner bite block member of the U-shaped mounting base of the dental bite block assembly of FIG. 1.
Figure 6:
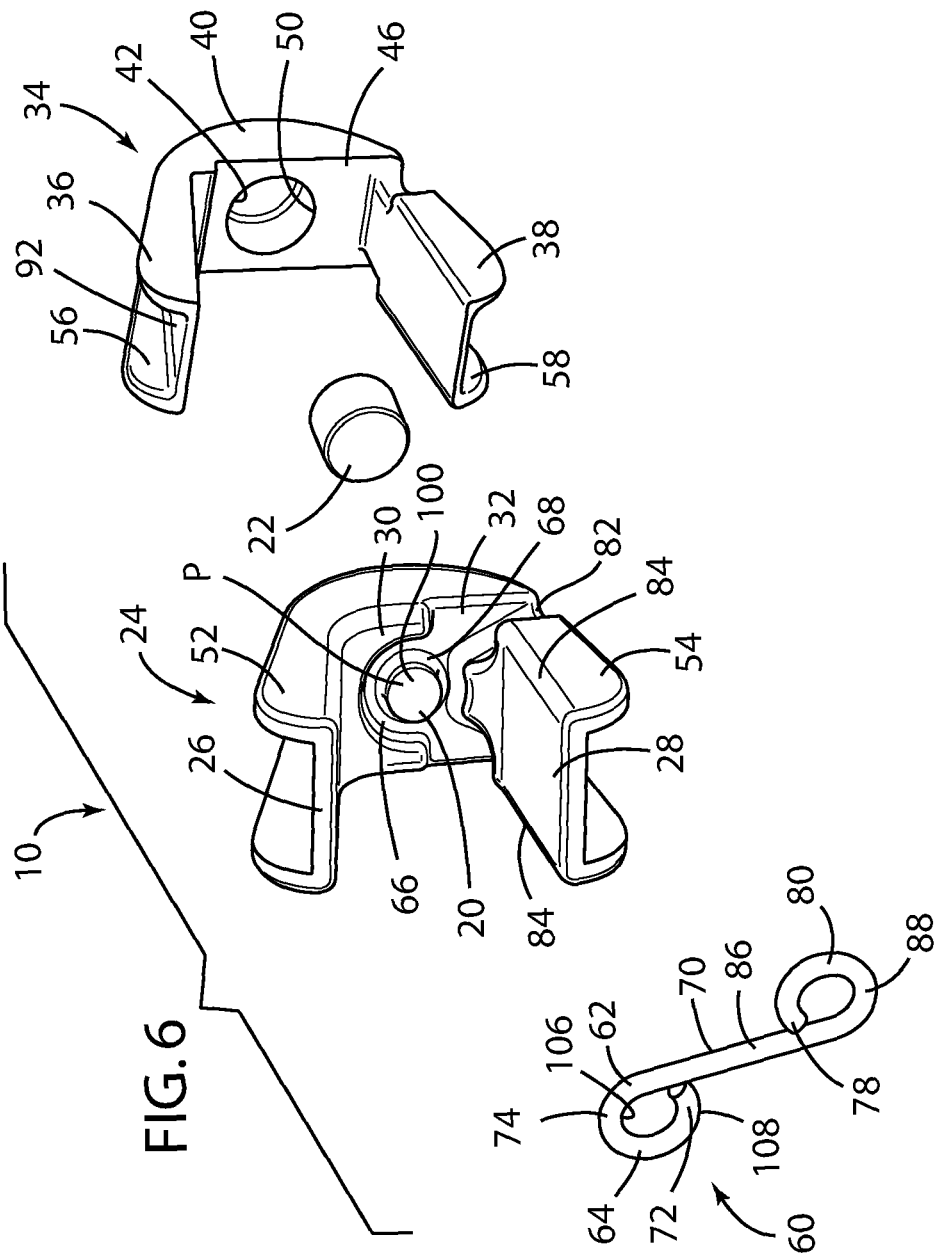
FIG. 6 is a front perspective exploded view of the dental bite block assembly of FIG. 1.
Figure 9:
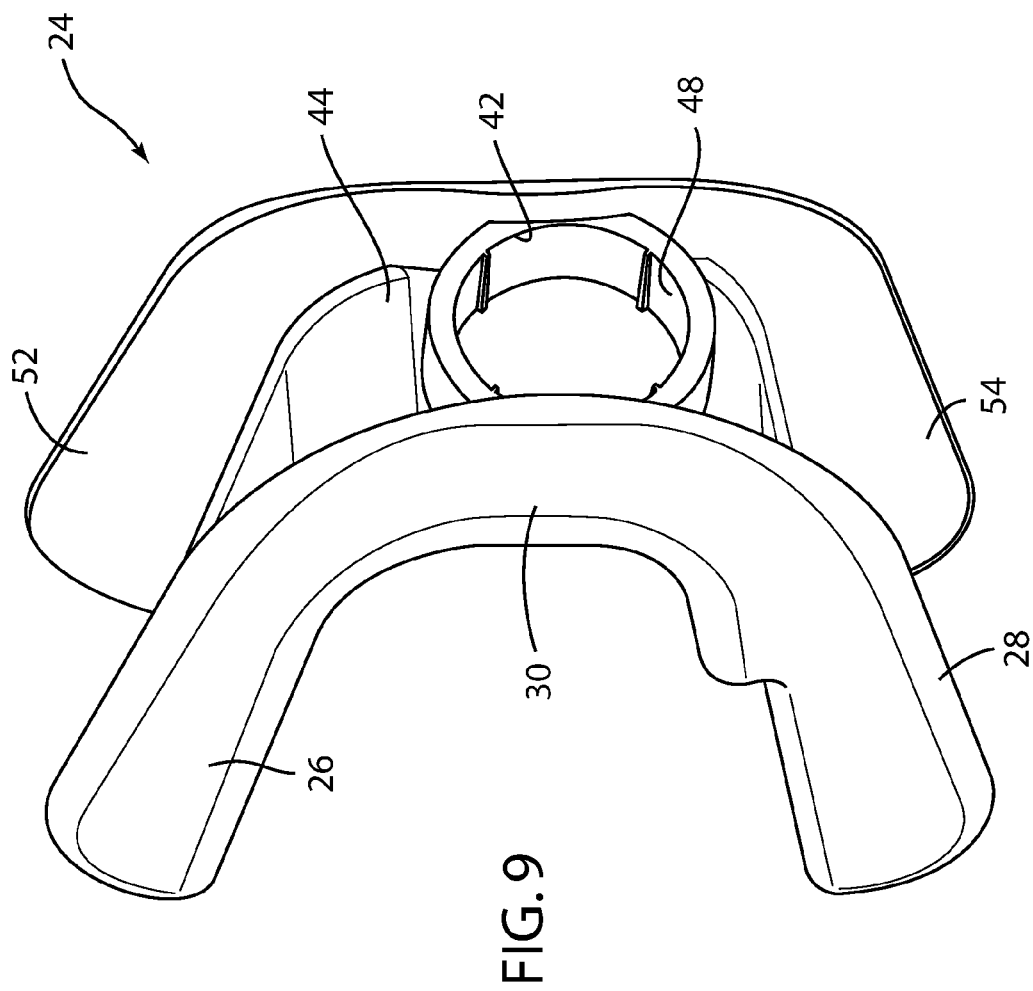
FIG. 9 is a rear perspective view of the inner bite block member of the U-shaped mounting base of the dental bite block assembly of FIG. 7.
Figures 14, 15:
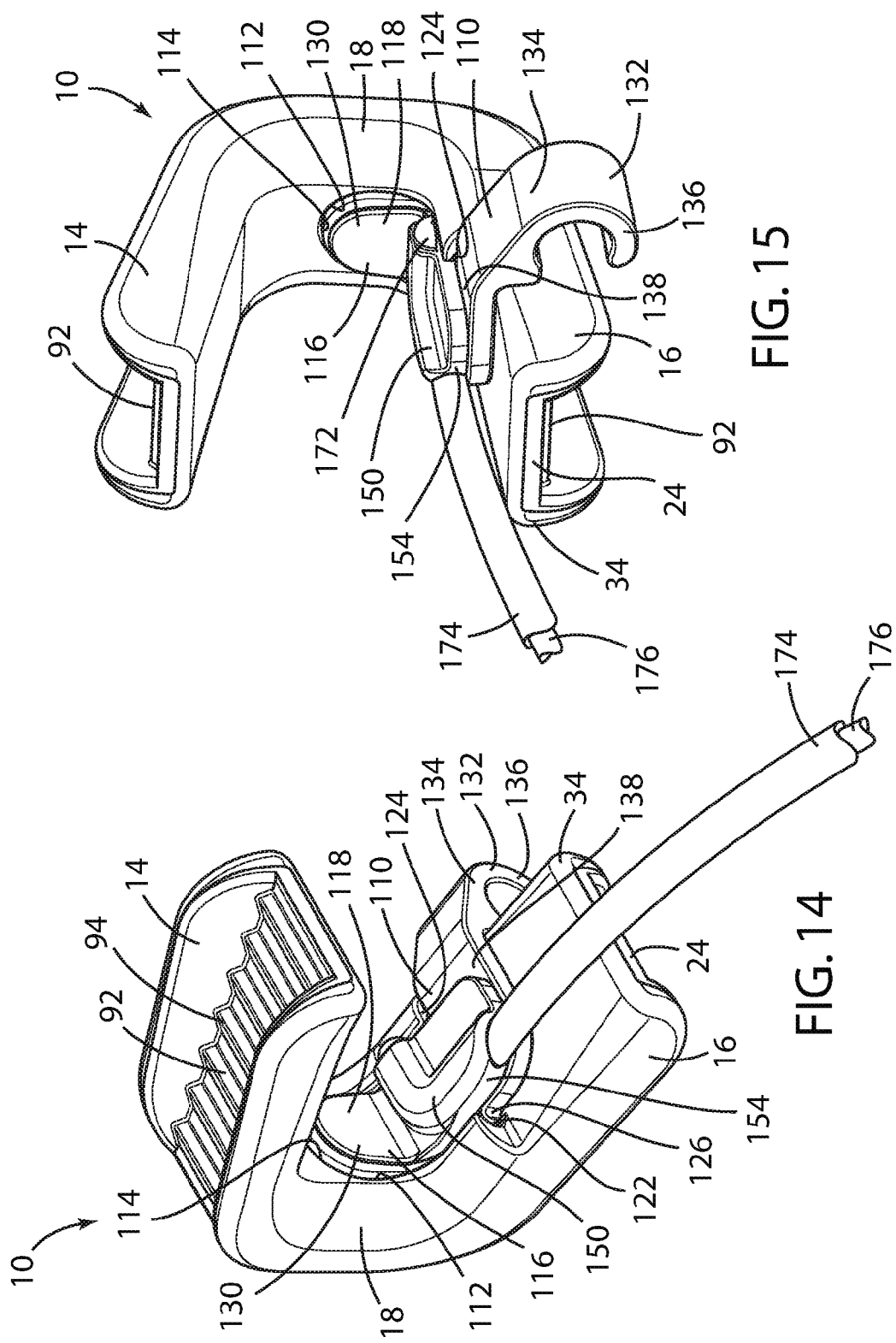
FIG. 14 is a front right perspective view of an additional embodiment of a dental bite block assembly of the present disclosure.
FIG. 15 is a front left perspective view of the dental bite block assembly of FIG. 14.

As further shown in FIGS. 1, 2, and 4, the central portion 18 of the U-shaped mounting base 12 is also provided with a retaining notch 82 disposed on at least one lateral edge 84 proximate the central portion 18 of the U-shaped mounting base 12. The dental accessory 60 preferably has a middle portion 86. After the curved portion 80 of the dental accessory 60 is inserted into and fittingly received within the torus 68 via axial motion, the middle portion 86 of the dental accessory 60 is disposed proximate the retaining notch 82. The dental accessory 60 is then rotated to a fully installed position, wherein the middle portion 86 of the dental accessory 60 is received within and engages the retaining notch 82.

Even more preferably, the central portion 18 of the U-shaped mounting base 12 has a lateral edge 84 on each side and a retaining notch 82 is disposed on each of the lateral edges 84 proximate the central portion 18 of the U-shaped mounting base 12. The dental accessory 60 is accordingly mountable on either side of the U-shaped mounting base 12. This is a significant feature, in that it allows the same U-shaped mounting base 12 and dental accessory 60 to be used on either side of the patient's mouth. The dental accessory 60 is thereby configured to be attached on either side of the U-shaped mounting base 12, depending upon which side of the patient's mouth the U-shaped mounting base 12 is situated.

The accessory mount 20 on the U-shaped mounting base 12 and dental bite block mount 62 on the dental accessory 60 together cooperate to make it simple and quick for the attending dentist and/or dental hygienist to attach, remove, or reposition an aspirating tube or tongue guard with one hand, as further described below. The disclosed dental bite block assembly 10 also helps with patient comfort, in that the dental accessory 60 can be quickly removed or repositioned in the event that the dental bite block assembly 10 becomes uncomfortable.

Figure 3:
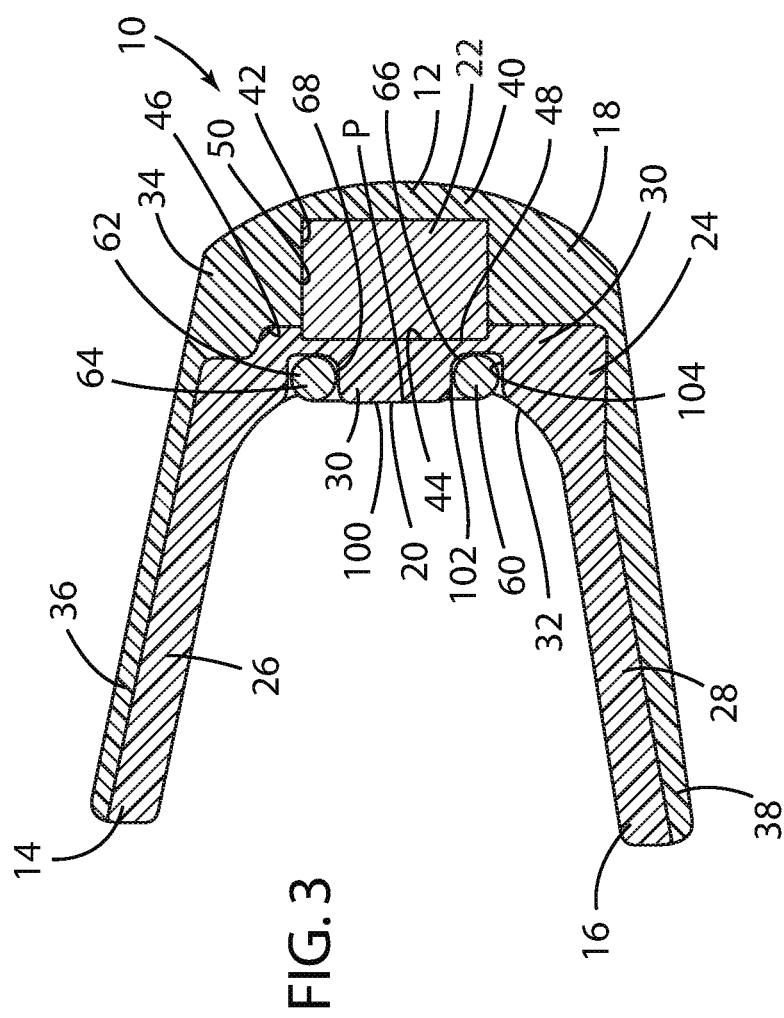
FIG. 3 is a side cross-sectional view of the dental bite block assembly of FIG. 1.

As shown in FIGS. 1 through 3, the dental bite block mount 62 of the dental accessory 60 comprises a ferromagnetic ring attachment at the first distal end 72. A saliva ejection tube holder 88 is disposed at the opposite second distal end 78 for receiving and holding a saliva ejection tube 90 below the accessory mount 20. With the dental bite block mount 62 of the dental accessory 60 attached to the accessory mount 20 of the U-shaped mounting base 12, an unobstructed area is provided to perform dental procedures proximate the dental bite block assembly 10, while at the same time providing for the evacuation of particulates or saliva from the patient's mouth through the saliva ejection tube 90 that is securely held in place at a desired location, as shown in FIG. 1.

Preferably, the dental accessory 60 forms a 6.35 mm loop on each end with a slight oval shape to fit the outer cross-sectional shape of the saliva ejection tube 90. More preferably still, the dental accessory 60 is constructed from stainless steel, so that it can be reused with an extended life through multiple autoclaving cycles. Alternatively, the dental accessory 60 can be constructed from a cold-rolled 3/32 steel rod that has been electroplated with nickel and 24-karat gold, with a bright nickel base of a thickness between 0.13 and 0.25 A$\mu$m, and then with 24-karat gold layer with a thickness between 0.13 and 0.25 A$\mu$m. With the dental accessory 60 being fabricated from stainless steel or cold-rolled steel and the U-shaped mounting base 12 being fabricated from plastic, along with the use of a high temperature permanent magnet as the first magnetically energetic material 22, the dental bite block assembly 10 of the present disclosure is particularly well-suited for high temperature sterilization via an autoclave for reuse of the components of the dental bite block assembly 10.

As an additional feature of the present disclosure, the dental accessory 60 is provided in a variety of sizes, where the length of the middle portion 86 of the dental accessory 60 and the diameter of the saliva ejection tube holder 88 is offered in a variety of sizes, such that virtually any diameter saliva ejection tube 90 may be used by selecting the appropriately sized dental accessory 60. Preferably, the saliva ejection tube holder 88 diameter varies from 28 mm to 34 mm.

In operation, it is merely necessary to position the U-shaped mounting base 12 between the upper and lower arcade of teeth of the patient on one side of the patient's arcades on either the right or the left side, depending upon the dental needs of the patient. Preferably, an outer surface 92 of the upper bite portion 36 and lower bite portion 38 of the outer bite block member 34 are each provided with a textured surface 94, as best shown in FIGS. 7 and 8, as a series of evenly raised ridges 94, to enhance the patient's bite on the U-shaped mounting base 12.

The dentist and/or dental hygienist then selects the appropriately sized dental accessory 60 having the desired diameter tube holder 88 at its second distal end 78 and inserts the smaller diameter end 96 of an saliva ejection tube 90 through the saliva ejection tube holder 88. The inlet end 98 of the saliva ejection tube 90 is typically flared and larger in diameter, as shown in FIG. 1. As noted above, the saliva ejection tube holder 88 is preferably slightly oval in shape to accommodate the oval shape of the saliva ejection tube 90 and lock it into position. That is, when the desired length or depth of the saliva ejection tube 90 is in position on the tube holder 88, the operator need merely twist the saliva ejection tube 90 a quarter of a turn to lock it into place on the tube holder 88. The smaller diameter end 96 of the saliva ejection tube 90 can then be attached to a vacuum valve hand piece (not shown). Because one end of the ejection tube is flared and the other is attached to the vacuum valve hand piece, the saliva ejection tube 90 cannot separate from tube holder 88 and is held securely thereon.

With the U-shaped mounting base 12 thus securely positioned in the patient's mouth, the dental accessory 60, which now includes the dental bite block mount 62 and the tube holder 88 within which the saliva ejection tube 90 is installed, is simply inserted into the patient's mouth using one hand. The magnetic field from the axially magnetized neodymium high curie temperature magnet as the first magnetically energetic material 22 in the U-shaped mounting base 12 attracts or "pulls" the dental bite block mount 62 toward the accessory mount 20 on the U-shaped mounting base 12 and into firm engagement with torus 68 of the accessory mount 20. The dental accessory 60 is then rotated so that the middle portion 86 of the dental accessory 60 is received within and engages the retaining notch 82. Thus, the dental bite block assembly 10 is capable of firmly holding the saliva ejection tube 90 in position, the saliva ejection tube 90 having been secured to the second distal end 78 of the curved portion 80 of the dental accessory 60.

In accordance with the present disclosure, the magnetization direction and different grades of magnets can be utilized to obtain attractive forces of a desired intensity. Additionally, the first magnetically energetic material 22 may be embedded into the central portion 18 of the U-shaped mounting base 12 at varying depths and locations to obtain specific desired attractive force intensity. Thus, it is possible to obtain varying "pull strength" of the U-shaped mounting base 12 relative the dental accessory 60. Moreover, it should be noted that the permanent magnet as the first magnetically energetic material 22 in the U-shaped mounting base 12 can be replaced with a steel ferromagnetic ring or object, which can be embedded into the polypropylene to cooperate with the accessory mount 20 to hold the dental accessory 60. In such a case, the dental bite block mount 62 formed by the curved portion 80 of the first distal and 72 of the dental accessory 60 can be fabricated from a permanent magnetic material for attachment to the accessory mount 20 of the U-shaped mounting base 12.

Preferably, the accessory mount 20 on the central portion 18 of the U-shaped mounting base 12 has a concentrically protruding portion 100 within the torus 68, wherein the concentrically protruding portion 100 forms the center of the torus 68. As noted above, the torus 68 has an inner diameter 102 and an outer diameter 104 that complements the inner diameter 106 and outer diameter 108 of the curved portion 74 at the first distal end 72 of the dental accessory 60 to help guide and hold the dental bite block mount 62 in place on either of the left or right side of the mounting base 12. The interface of the torus 68 and the curved portion 74 of the first distal end 72 of the dental accessory 60 provides a pivot point P about which the dental accessory 60 may be rotated into engagement with retaining notch 82 on either lateral edge 84 on the U-shaped mounting base 12. Thus, the dental accessory 60 and the saliva ejection tube 90 can be effectively locked into place on the U-shaped mounting base 12 to prevent the saliva ejection tube 90 from inadvertently moving within the patient's mouth.

To remove the dental accessory 60 and attached saliva ejection tube 90, the dental accessory 60 is slightly rotated about the concentrically protruding portion 100 and the pivot point P by the operator with one hand to free the middle portion 86 of the dental accessory 60 from engagement with the retaining notch 82. With the dental accessory 60 unlocked from the U-shaped mounting base 12, the dental accessory 60 can be pulled straight out and away from accessory mount 20 on the U-shaped mounting base 12. The dental accessory 60 and the attached saliva ejection tube 90 can then be readily removed from the patient's mouth.

The dental bite block assembly 10 of the present disclosure thus makes it simple, easy, and quick to attach, remove or re-position the saliva ejection tube 90 by the operator using only with one hand. This feature has the advantage of allowing a dentist and/or dental hygienist to work independently without the need for an assistant. The disclosed dental accessory 60 also extends and positions the inlet end 98 saliva ejection tube 90 below the U-shaped mounting base 12, allowing for an unobstructed area to perform dental procedures, while at the same time allowing the saliva ejection tube 90 to be positioned to effectively evacuate particulates or saliva from the patient's mouth.

Further, any diameter saliva ejection tube 90 may be used by selecting a dental accessory 60 having an appropriately sized saliva ejection tube holder 88. The design of the U-shaped mounting base 12 in the dental accessory 60 enables higher tempered sterilizations by autoclave without affecting the performance of the axially magnetized neodymium high curie temperature magnet. In addition, the disclosed U-shaped mounting base 12 and dental accessory 60 present few sharp or jagged edges for bacteria to get caught in. Since the saliva ejection tube holder 88 is either fabricated from stainless steel or cold-rolled steel that is electroplated with bright nickel and 24-karat gold to prohibit corrosion, high temperature sterilization is allowed for reused as needed.

Additionally, it should be noted that the U-shaped mounting base 12 of the dental bite block assembly 10 disclosed herein may also be used for holding dental accessories and instruments other than a saliva ejection tube 90 in position within the mouth. For example, the U-shaped mounting base 12 and a dental accessory having an enlarged saliva ejection tube holder 88 may be used to position and hold an endoscope in place.

The description of the preceding embodiment presents a dental bite block assembly 10 that preferably uses a ferromagnetic ring on the curved portion 74 on the dental accessory 60 as the dental bite block mount 62 in conjunction with in a high curie temperature axially magnetized neodymium magnet as the first magnetically energetic material 22 embedded into a U-shaped mounting base 12. However, alternative embodiments can be employed to hold not only a saliva ejection tube 90, but a tongue suppressor and a light delivery system, as disclosed herein.

For example, a second embodiment of a second dental accessory 110 is shown in FIGS. 7 and 8. In this embodiment, an accessory mount 112 is similarly disposed on the central portion 18 of the U-shaped mounting base 12, but in this case comprises a forwardly facing recess 114 is disposed proximate the first magnetically energetic material 22 embedded in the central portion 18. The dental bite block mount 116 of the dental accessory 110 in this embodiment comprises a rearwardly facing member 118 within which the second magnetically energetic material 64 is disposed, wherein the rearwardly facing member 118 of the second dental accessory 110 is fittingly received within the forward facing recess 114 of the central portion 18 of the U-shaped mounting base 12. Preferably, in this embodiment, both the first and the second magnetically energetic materials 22, 64 in the central portion 18 of the U-shaped mounting base 12 and the second dental accessory 110, respectively, are both a permanent magnet formed of an axially magnetized neodymium high curie temperature magnet and oriented in complementary pole relationship, such that the S and N poles are disposed in adjacent and abutting relation.

The forward facing recess 114 in the central portion 18 of the U-shaped mounting base 12 preferably has a semicircular configuration, that is, forward facing recess 114 is a semicircular recess that has an open lower portion 120, thereof and the lower bite portion 16 of the U-shaped mounting base 12 comprises a pair of channels 122, 124 extending forwardly on each lateral side 84 of the lower bite portion 16 of the U-shaped mounting base 12 proximate the open lower portion 120 of the semicircular forward facing recess 114. One of a pair of locking tabs 126, 128 is disposed on each lateral side 18 of the second dental accessory 110 proximate the rearwardly facing member 118, where one of each of the locking tabs 126, 128 is slidingly received within of one of the channels 122, 124.

Figure 16:
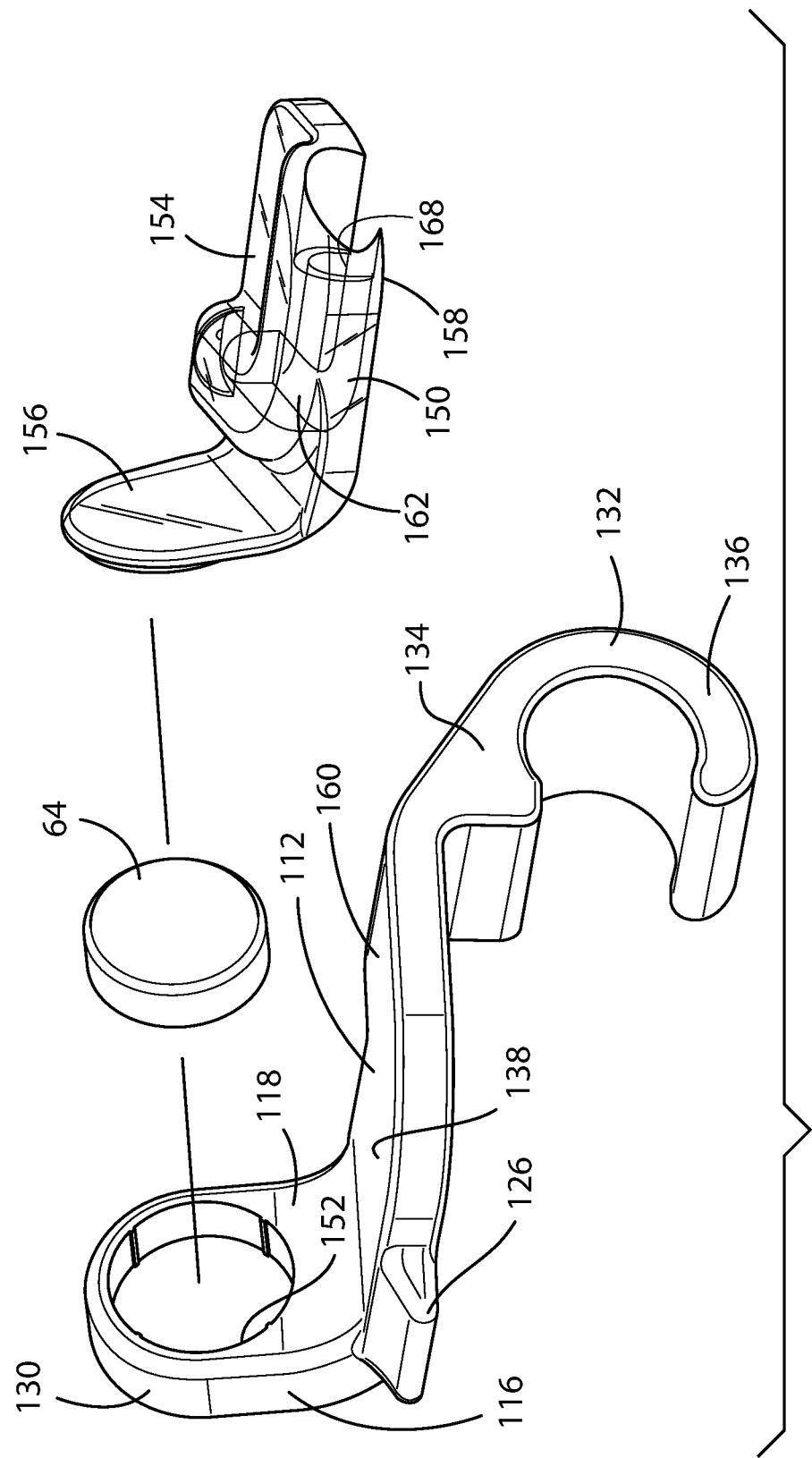
FIG. 16 is a exploded front perspective view of the dental accessory and light mount for an illuminated dental accessory of FIG. 14.
Figure 20:
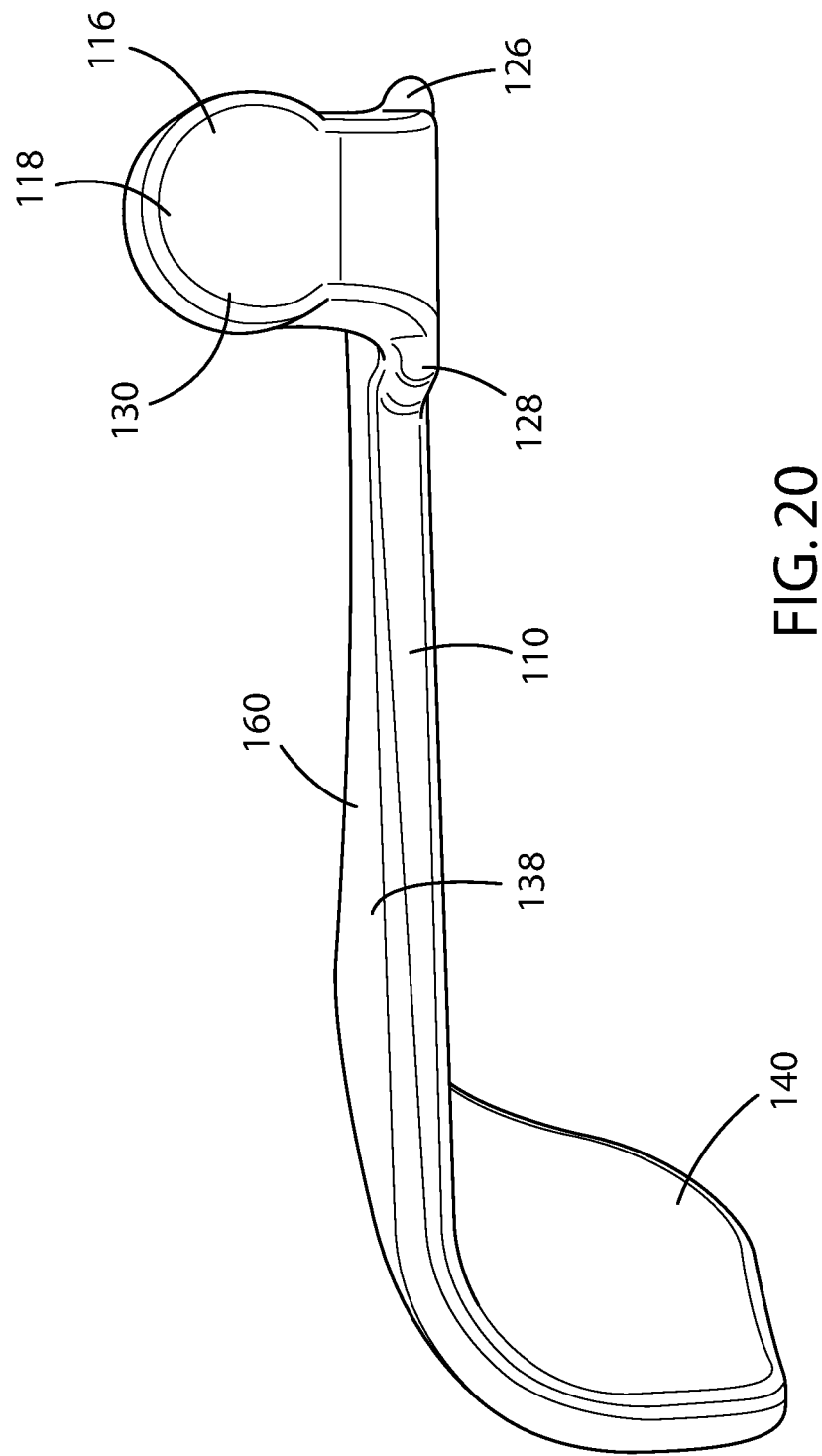
FIG. 20 is a rear plan view of the dental accessory for the dental bite block assembly of FIG. 19.

The locking tabs 126, 128, which extend laterally outwardly, can have varying configurations. In one configuration, the locking tabs 126, 128 can have a triangular or wedge-shape, as shown in FIG. 16. In another configuration, the locking tabs 126, 128 can have a semicircular shape, as shown in FIG. 20. Importantly, the locking tabs 126, 128 must be sized to be fittingly received within the channels 122, 124, so as to prevent the second dental accessory 110 from moving or rocking relative to the U-shaped mounting base 12 once mounted therein.

Preferably, the semicircular forward facing recess 114 in the central portion 18 of the U-shaped mounting base 12 is concentrically disposed proximate the first magnetically energetic material 22 embedded in the central portion 18 of the U-shaped mounting base 12. The rearwardly facing member 118 of the dental bite block mount 116, within which the second magnetically energetic material 64 is disposed, comprises a semicircular projection 130 that is fittingly received within the semicircular forward facing recess 114 of the central portion 18 of the U-shaped mounting base 12.

As in the first embodiment, the U-shaped mounting base 12 is first positioned in the patient's mouth. The second dental accessory 110 of the second embodiment, which includes the dental bite block mount 116 and a tube holder clasp 132, within which the saliva ejection tube 90 is installed, are then simply placed into the patient's mouth using one hand. The mutually attractive magnetic fields from each of the axially magnetized neodymium high curie temperature magnets that comprise the first and second magnetically energetic materials 22, 64, preferably embedded in both the U-shaped mounting base 12 and second dental accessory 110, attracts or "pulls" the dental bite block mount 116 formed on the semicircular projection 130 of the second dental accessory 110 into firm engagement within the semicircular forward facing recess 114 of the accessory mount 112 on the U-shaped mounting base 12 and the locking tabs 126, 128 into firm engagement with the channels 122, 124. Thus, the dental bite block accessory 10 firmly and securely holds the saliva ejection tube 90, which is secured to the second dental accessory 110, in position.

Further, as shown in FIGS. 7 and 8, the tube holder clasp 132 of the second dental accessory 110 further comprises a laterally extending curved portion 134 that terminates at a flexible ring 136 for receiving a dental tool, such as the saliva ejection tube 90, described above. As in the first embodiment, in such case the second dental accessory 110 can be provided with a number of different sizes of the flexible ring 136 for receiving saliva ejection tubes 90 of varying sizes, as noted above. As shown, the flexible ring 136 is mounted to the laterally extending curved portion 134 that extends laterally away from and below a main body 138 of the second dental accessory 110 in a gradual curve downwardly, so as to position the saliva ejection tube 90 below the U-shaped mounting base 12. As noted above, this provides access to the patient's mouth for the dentist and/or dental hygienist without interference by the saliva ejection tube 90. It should be understood that mirror image right side and left side dental accessories 110 can be provided for use on either the right or the left side of the same U-shaped mounting base 12, the U-shaped mounted base 12 being disposed on either side of the patient's mouth as required.

Figure 19:
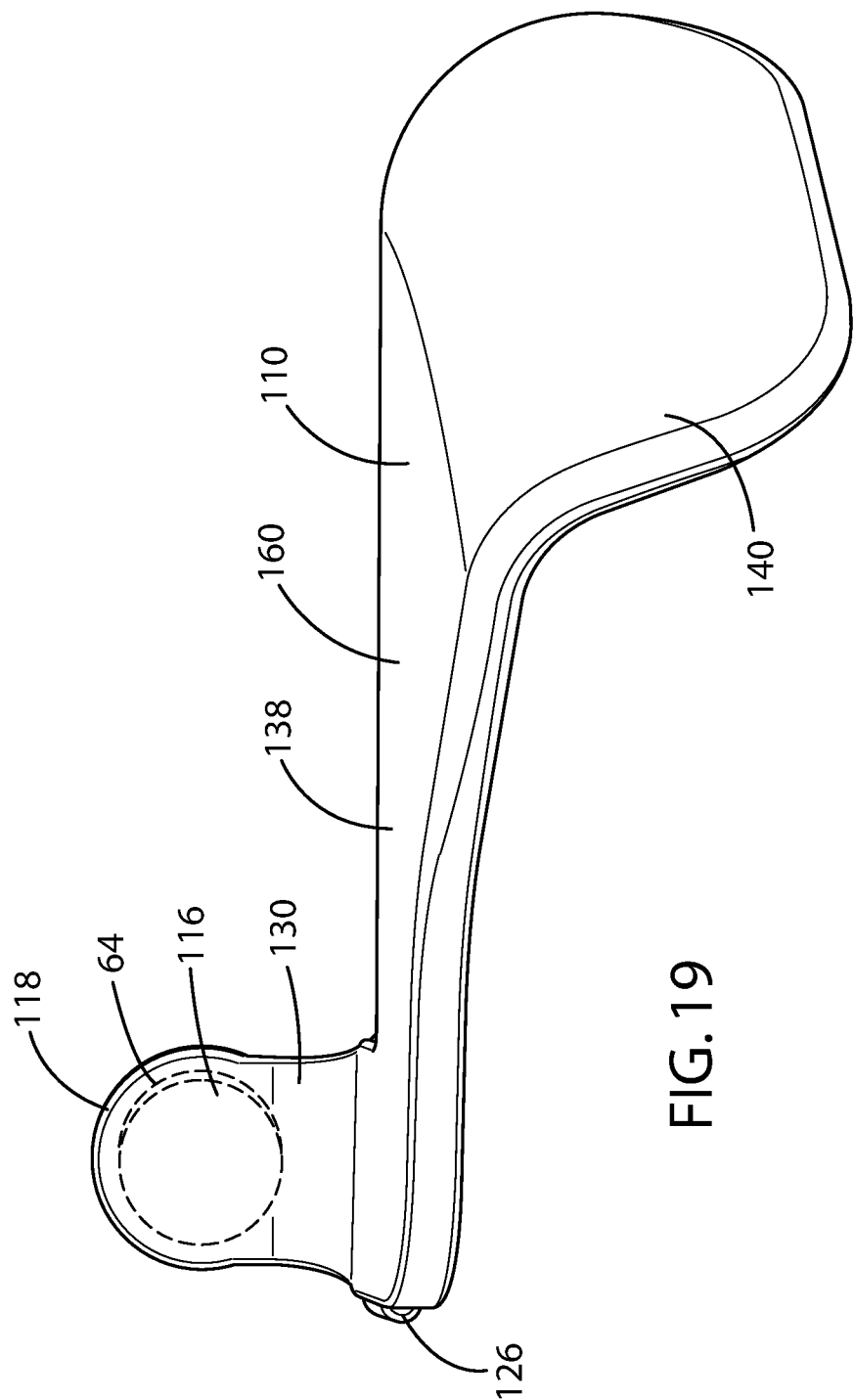
FIG. 19 is a front plan view of an additional embodiment of a dental accessory for the dental bite block assembly of the present disclosure.
Figure 21:
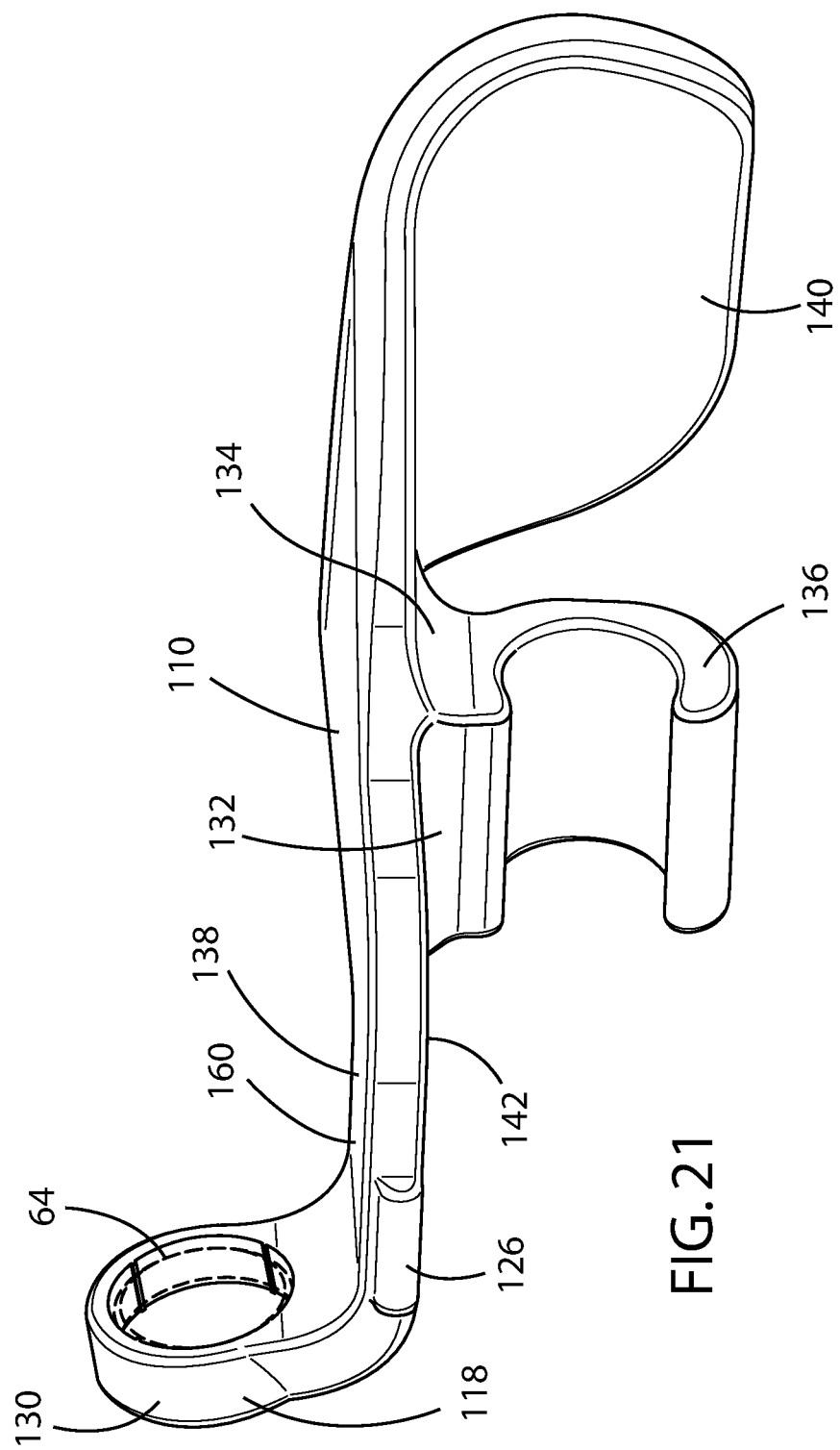
FIG. 21 is a front perspective view of an still another embodiment of a dental accessory for the dental bite block assembly of the present disclosure.
Figure 22:
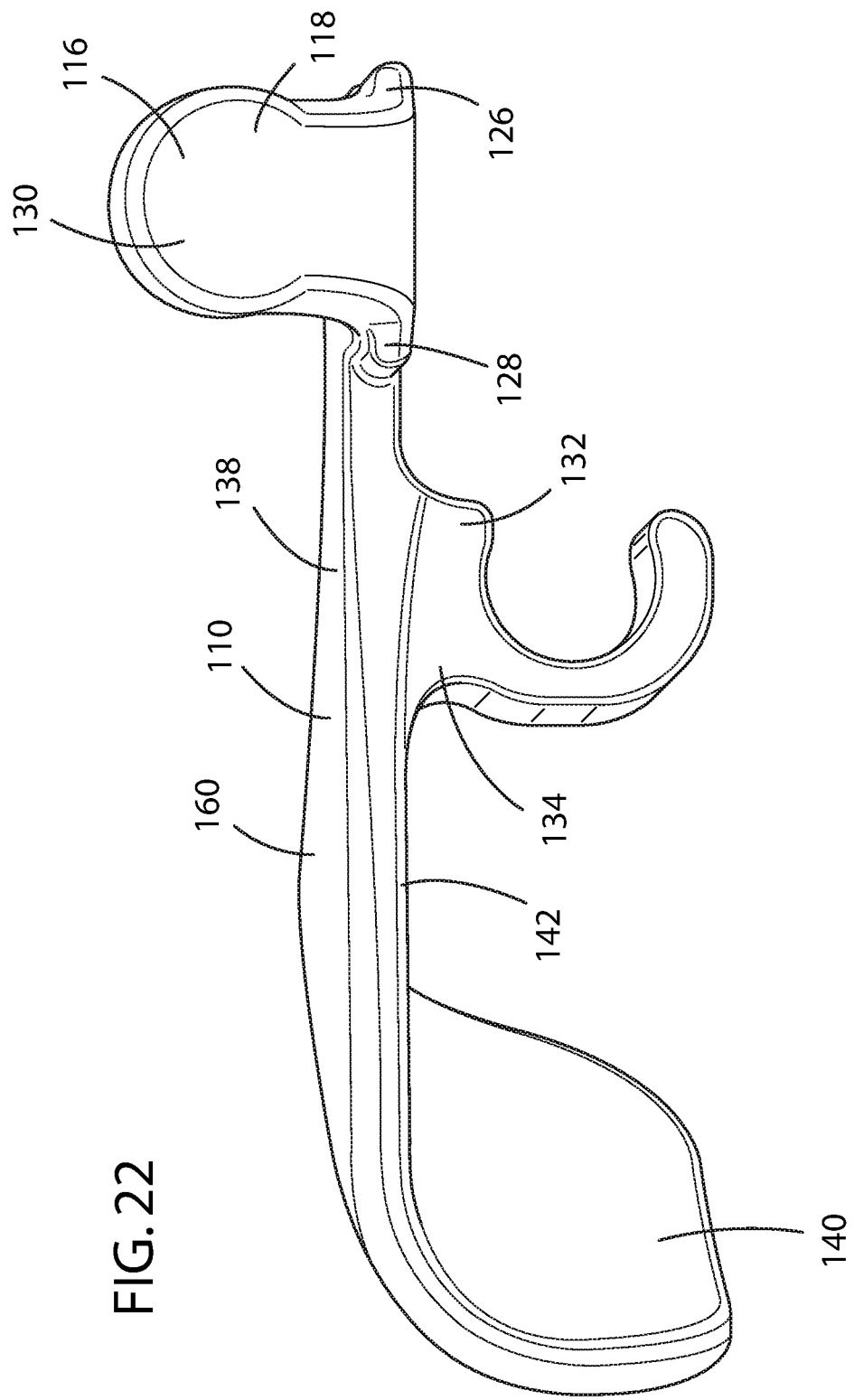
FIG. 22 is a rear perspective view of the dental accessory of FIG. 21.
Figure 23:
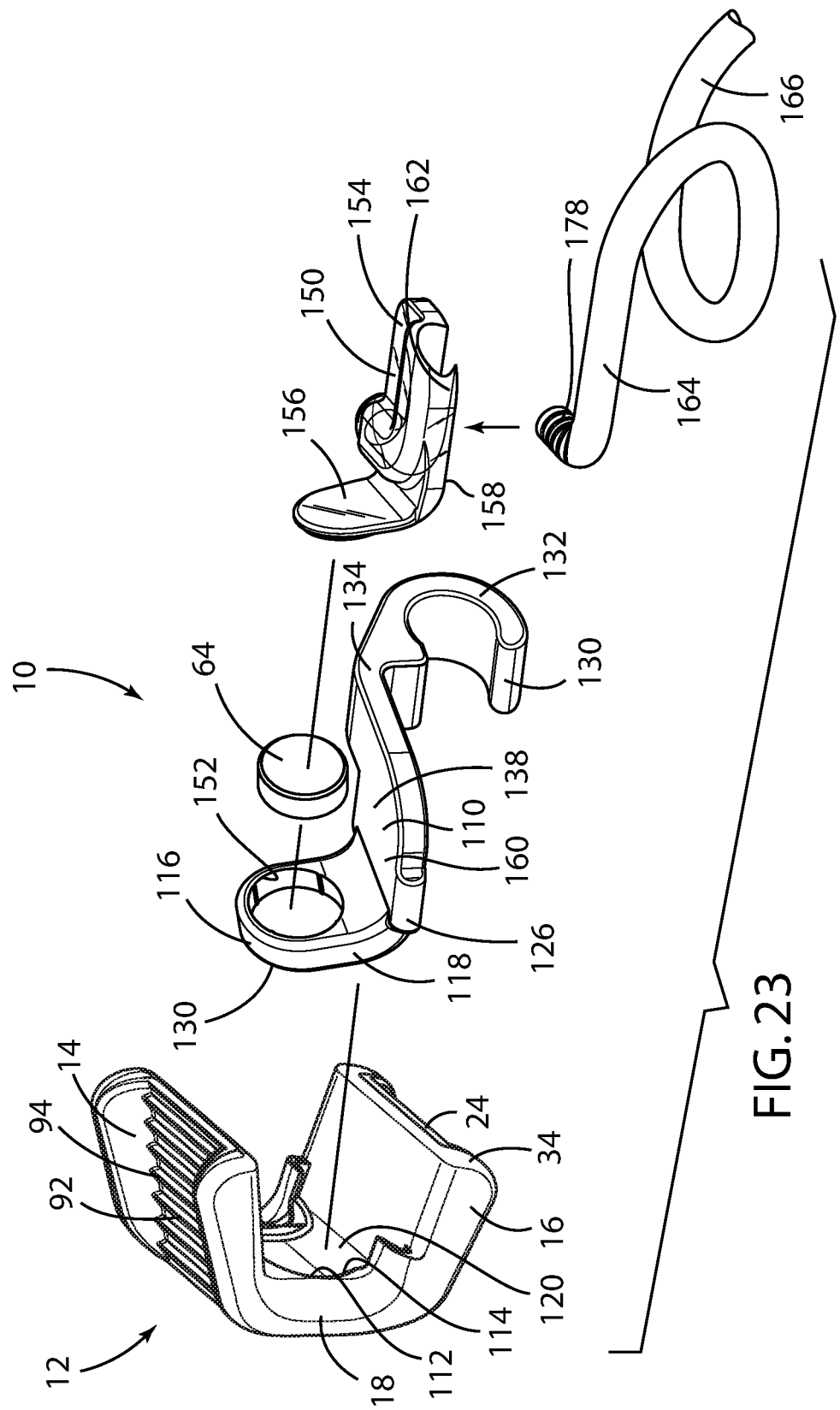
FIG. 23 is an exploded view of the dental bite block assembly equipped to utilize a light delivery system of the present disclosure.

In still a further embodiment of the present disclosure, as shown in FIGS. 19 and 20, the second dental accessory 110 can include a tongue suppressor 140 to protect a patient tongue. As shown, the tongue suppressor 140 extends laterally from the main body 138 of the second dental accessory 110 from a laterally extending curved portion 134 downward so as to position the tongue suppressor 140 below the U-shaped mounting base 12. Again, this provides access to the patient's mouth for the dentist or dental hygienist without interference by the tongue suppressor 140. As shown in FIGS. 21 and 22, the dental accessory can also include a tube holder clasp 132 depending from a lower portion 142 of the tongue suppressor 140, which will function as described above.

In yet another embodiment of the present invention, the dental accessory can include an LED light attachment point 150 to assist in illumination in the mouth. As noted below, the LED light attachment point 150 can be used alone, or combined with a dental accessory 60, 110 that includes either or both of the tube holder clasp 132 and/or tongue suppressor 140. When employing the LED light attachment point 150, the U-shaped mounting base 12, particularly the inner bite block member 24, is preferably fabricated from a clear plastic material that, when exposed to a source of intense light, effectively becomes an illumination device within the patient's mouth. One such material appropriate for use in this illuminated application is polymethyl methacrylate (PMMA), which provides very good light transmission throughout the structure of any article manufactured therefrom. This is particularly appropriate for use in the fabrication of the dental accessory 60, 110, when the dental accessory 60, 110 includes a tongue suppressor 140, as noted above.

In the embodiment employing an LED light attachment point 150, the second dental accessory 110 is preferably constructed as in the second embodiment above, that is, with a semicircular projection 130 that is received within a semicircular forward facing recess 114 in the central portion 18 of the U-shaped mounting base 12. The second dental accessory 110 is provided with a forward facing recess 152 formed in the semicircular projection 130, within which the permanent magnet as the second magnetically energetic material 64 is received prior to assembly of the dental accessory 110. A light mount 154, which also has a complementary semicircular projection 156, has a substantially flat lower surface 158 upon which it is fittingly received on a flat mounting base 160 of the main body 138 the dental accessory 110. The flat mounting base 160 is preferably substantially the same area as that of the flat lower surface 158.

Light mount 154 is preferably attached to the flat mounting base 160 of the second dental accessory 110 via a thin layer of a liquid optically clear (LOC) adhesive (not shown) that is cured by UV radiation. Once positioned on the flat mounting base 160 of the second dental accessory 110 with the LOC adhesive in place, the light mount 154 is permanently attached to the second dental accessory 110 via exposure to ultraviolet (UV) light radiation to cure the adhesive. With the permanent magnet 248 that forms the second magnetically energetic material 64 sandwiched between the semicircular projections 130, 156 in both the second dental accessory 110 and the light mount 154, the permanent magnet 248 is sealingly encased within the forward facing recess 152.

The light mount 154 is preferably provided with an L-shaped recess or cavity 162 on the flat lower surface 158, within which is received a first distal end 164 of an accessory fiber optic cable 166. Preferably, the accessory fiber optic cable 166 is approximately 2.5 mm in diameter and is preferably comprised of any suitable material for use in plastic optical fibers, and more preferred is 2.5 mm solid core side-glow single mode fiber optic cable fabricated of PMMA. Alternatively, a 2.5 mm solid core end-glow fiber optic cable fabricated of PMMA can be employed.

The L-shaped recess or cavity 162 similarly has an inner diameter of approximately 2 mm in diameter, so as to fittingly receive the first distal end 164 of the accessory fiber optic cable 166. The L-shaped recess 162 has a corresponding L-shaped opening 168 on the flat lower surface 158 of the light mount 154 that is slightly smaller in width then the outer diameter of the accessory fiber optic cable 166 that opens into an L-shaped recess 162, such that the first distal end 164 of the accessory fiber optic cable 166 can be bent into an L-shape and then pressed or snapped into the L-shaped opening 168 and received within the L-shaped recess 162 to secure the first distal end 164 of the accessory fiber optic cable 166 within the light mount 154. Preferably, the first distal end 164 of the accessory fiber optic cable 166 is disposed in abutting relation with and against a semispherical bulb 172 that is incorporated within the structure of the light mount 154 and which acts as a light diffuser. Thus, light can be provided within a large portion of the patient's mouth without undue clutter therein.

Preferably, the accessory fiber optic cable 166 is clad with an outer cladding 174 having an index of refraction higher or lower than that of the index of refraction of its core 176 and the outer cladding 176 at the first distal end 164 of the accessory fiber optic cable 166 is scored or cut completely around the outer circumference of the outer cladding 174 to form score rings 178 to expose the core 176 material. Thus, as light is introduced to the accessory fiber optic cable 166, it escapes through the score rings 178 within the L-shaped recess 162 within the light mount 154 and is diffused 360° throughout the light mount 154. Because the light mount 154 is attached to the second dental accessory 110 via an LOC adhesive, the light is further transmitted to and throughout the second dental accessory 110 and the U-shaped mounting base 12 to which it is attached. Preferably, six to ten such scored rings are provided within the L-shaped recess 162 of the light mount 154. More or less light can be controlled by varying the number of score rings 178 presented.

The light source to the fiber optic cable can be provided a number of ways. However, it is preferred that a light engine 200 offered by Olight, Shenzhen, China, I as Model No. SR52-UT Intimidator be employed (found at https://olightworld.com/store/flashlight/sr52-ut-intimidator.html). This light engine 200 features a Cree XP-L HI LED light source 202 with a maximum output of 1100 lumens. This light engine 200 offers three brightness levels: 1100 lumens, 550 lumens, in 80 lumens. As this light engine 200 develops a significant amount of heat, the light engine 200 is preferably modified, replacing its original tempered glass lens with an aluminum heat dissipater 204 having an upper end 206 and a lower end 208, as shown in FIG. 26. Preferably, the aluminum heat dissipater 204 maintains the light engine at 120° F. or lower to maintain the high level of light generated for long periods of time, such as of 20 to 40 minutes. Thermal management is critical in maintaining a high level of light output, while also reducing thermal exposure to the batteries, fiber optic light cable, and preventing component and battery failure.

Figure 28A:
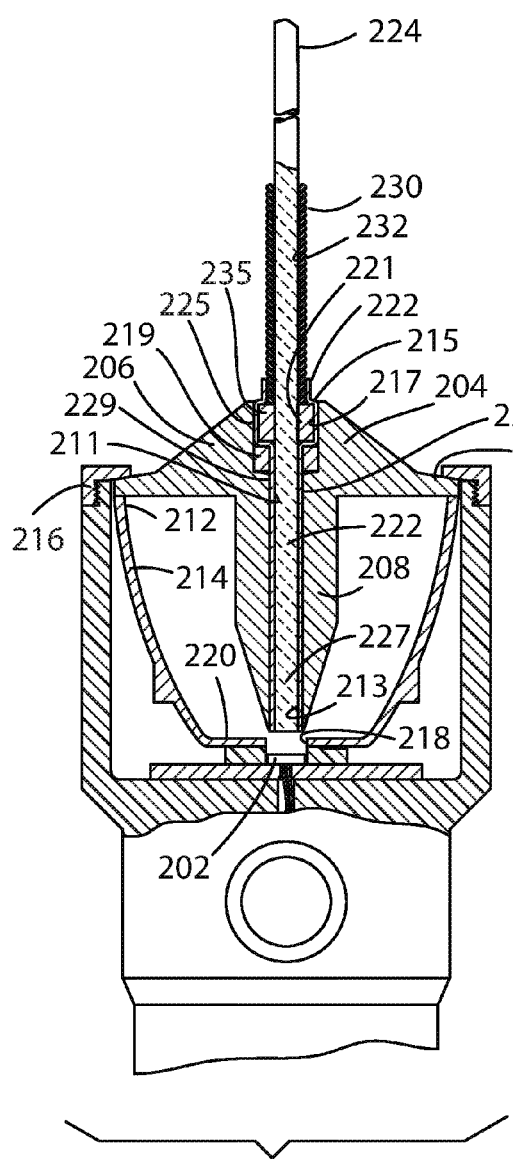
FIG. 28A is a partial cross-sectional view of the assembled light engine of the light delivery system for the dental bite block assembly of FIG. 24.
Figure 28B:
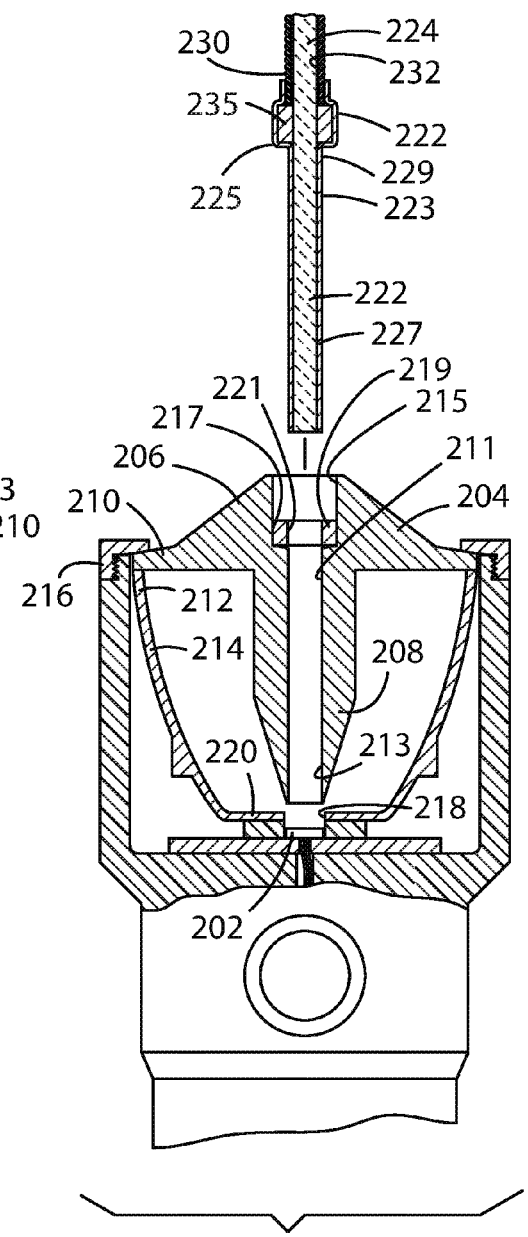
FIG. 28B is a partial cross-sectional view of the disassembled light engine of the light delivery system for the dental bite block assembly of FIG. 24.

The upper end 206 of the aluminum heat dissipater 204 is fabricated from 6061 grade aluminum and is thus readily machined into the shape shown in FIGS. 28A and 28B, and is formed with a collar 210 that extends concentrically about the aluminum heat dissipater 204 and is supported by an upper edge 212 of the reflector 214 of the light engine 200. A threaded ring 216, which is normally used to retain the tempered glass lens against the reflector 214 in an unmodified light engine 200, is reinstalled to secure and sealingly mount the aluminum heat dissipater 204 in position, where the collar 210 preferably has a thickness that is substantially the same as the discarded tempered glass lens, as shown in FIGS. 28A and 28B.

The lower end 208 of the aluminum heat dissipater 204 is positioned proximate a bottom opening 218 at the base 220 of the reflector 214 and within a few millimeters, preferably 2 mm, of the LED 202 of the light engine 200. A passage 211 is machined through the aluminum heat dissipater 204 and forms a throughway between an opening 213 at the upper end 206 of the aluminum heat dissipater 204 proximate the bottom opening 218 at the base 220 of the reflector 214 and an opening 215 at the lower end 208 of the aluminum heat dissipater 204. A countersunk cavity 217 is formed at the upper end 206 of the aluminum heat dissipater 204 concentric with the opening 215 within which a magnet 219 having an axial concentric opening 221 is received and affixed.

An exposed first distal end 222 of a supply fiber optic cable 224 extends through and is fixedly restrained within a removable conduit 223, preferably fabricated from a large stainless steel hypodermic needle. The outer diameter of the removable conduit 223 is just slightly smaller than the inner diameter of the passage 211 within the aluminum heat dissipater 204, whereby the removable conduit 223 may be fittingly and slidingly received within the passage 211. Preferably, a short length of the supply fiber optic cable 224 extends beyond a lower portion 227 of the removable conduit 223. The supply fiber optic cable 224 is similarly preferably comprised of 2 mm solid core side glow fiber optic cable fabricated of PMMA. Preferably, the supply fiber optic cable 224 is approximately 3 meters long in order to allow maximum flexibility of its application. An upper portion 229 of the removable conduit 223 is provided with a clamp 225 that extends around the outer circumference of the supply fiber optic cable 224 and that is mechanically crimped (preferably in an octagonal pattern) into position to fixedly restrain the first distal end 222 of the supply fiber optic cable 224 within the removable conduit 223. The clamp 225 is preferably fabricated from a magnetic or a ferromagnetic material so as to be attracted to the magnet 219. As shown in FIGS. 28A and 28B, preferably a magnet 235 is mounted in the clamp 225 and disposed about the first distal end 222 of the supply fiber optic cable 224. Thus, when the removable conduit 223 is fully inserted within the passage 211 of the aluminum heat dissipater 204, the magnet 219 and the clamp 225 cooperate to restrain the removable conduit 223 and the exposed first distal end 222 of the supply fiber optic cable 224 in position. Alternatively, a collet (not shown) may be attached to a threaded conical flange (not shown) on the upper end 206 of the aluminum heat dissipater 204 through which the first distal end 222 of the supply fiber optic cable passes and is secured.

Thus, the exposed first distal end 222 of the supply fiber optic cable 224 is preferably disposed within the bottom opening 218 and proximate the lower end 208 of the aluminum heat dissipater 204. The exposed first distal end 222 of the supply fiber optic cable 224 is thus also positioned preferably 2 mm away from the LED light source 202. The supply fiber optic cable 224 is then passed through the passage 211 within the aluminum heat dissipater 204 and exits the upper end 206 of the aluminum heat dissipater 204 via opening 215. A strain relief spring 230 is likewise mechanically coupled with the clamp 225 and is disposed about a portion 232 of the supply fiber optic cable 224 as it exits the opening 228 of the upper end 206 of the aluminum heat dissipater 204, which prevents the supply fiber optic cable 224 from bending at a small radius (e.g., less than a 15 mm radius) and thereby prolongs supply fiber optic cable 224 life.

By virtue of the cooperation between the magnet 219 and clamp 225, the strain relief spring 230 and the supply fiber optic cable 224 are allowed to rotate 360° relative the vertical axis of the aluminum heat dissipater 204, so as to prevent tangling and binding of the supply fiber optic cable 224 while it is in use. In addition, removal of the removable conduit 223 from the passage 211 and reinsertion of the removable conduit 223 into the passage 211 can be simply and readily accomplished with one-hand operation of the user. When so reinserted, the exposed first distal end 222 of the supply fiber optic cable 224 is precisely positioned over the LED 202 without fail.

Also, it is been found that the LED 202 generates a significant amount of heat energy and the aluminum heat dissipater 204 is useful in forming a pathway for this heat energy to flow from the LED 202 and its associated components to the environment. The aluminum heat dissipater 204 is thus assembled to the light engine 200 with a thermal grease (sometimes referred to as CPU grease, heat paste, heat sink compound, heat sink paste, thermal compound, thermal gel, thermal interface material, thermal paste, or grey goo) to provide a thermally conductive (but usually electrically insulating) interface. Such an interface is commonly used between heat sinks and heat sources, for example, in high-power semiconductor devices. The thermal grease is believed to eliminate air gaps or spaces, which act as a thermal insulator, from the interface area so to maximize heat transfer. This promotes a heat energy flow path away from the LED 202 and light engine 200 to reduce temperatures.

An opposite second distal end 234 of the supply fiber optic cable 224 is preferably attached to a magnetic light coupler 236. The magnetic light coupler 236 has a first half 238 and a second half 240, where the first half 238 comprises a polycarbonate cylindrical body 242 having an open cylindrical cavity 244 having an inner diameter and a circular base 246 proximate the open cylindrical cavity 244 within which is mounted a permanent magnet 248. The cylindrical body 242 is coupled with the second distal end 234 of the supply fiber optic cable 224 via a sheath assembly 250, the sheath assembly 250 having an enlarged portion 252 having an outer diameter 254 similar to the outer diameter 256 of the circular base 246 and disposed proximate the permanent magnet 248, about which both the cylindrical body 242 is molded and encapsulated.

The permanent magnet 248 and the circular base 246 are each provided with a concentric opening 258, 260 through and within which the opposite second distal end 234 of the supply fiber optic cable 224 is received, wherein a face 262 of the second distal end 234 of the supply fiber optic cable 224 is fully exposed. The second distal end 234 of the supply fiber optic cable 224 is clamped in situ via the sheath assembly 250 and is thus prevented from separating from the first half 238 of the magnetic light coupler 236. The permanent magnet 248 and second distal end 234 of the supply fiber optic cable 224 is thus encased in a clear plastic to permanently secure the permanent magnet 248 therein and to otherwise enclose the second distal end 234 of the supply fiber optic cable 224, while maintaining an exposed face 262 at the second distal end 234 of the supply fiber optic cable 224.

Preferably, an alligator clip 264 is attached to the sheath assembly 250, whereby the first half 238 of the magnetic light coupler 236 can be readily attached to and detached from an article of clothing of the dentist, dental hygienist, and/or patient. Thus, the light engine 200 and the first end of the magnetic light coupler 236 can be essentially worn as part of a garment of the dental care provider.

The second half 240 of the magnetic light coupler 236 preferably comprises a substantially solid cylindrical body 266 having an outer diameter 268 that is slightly smaller than the inner diameter 270 of the open cylindrical cavity 244 of the first half 238 of the magnetic light coupler 236. The second half 240 of the magnetic light coupler 236 similarly has a cooperating permanent magnet 272, and a second distal end 274 of the accessory fiber optic cable 166, opposite the first distal end 164 of the accessory fiber optic cable 166 which is attached to the light mount 154, discussed above, is encapsulated within and permanently attached to the solid cylindrical body 266 of the second half 240 of magnetic light coupler 236. The permanent magnetic 272 similarly has a concentric opening 276 within which the second distal end 274 of the accessory fiber optic cable 166 is received and through which the second distal end 274 of the accessory fiber optic cable 166 is received and mounted, as noted above.

The solid cylindrical body 266 of the second half 240 of the magnetic light coupler 236 is received within the open cylindrical cavity 244 of the first half 238 of the magnetic light coupler 236 to assemble the magnetic light coupler 236. Preferably, the abutting face 278 of the second half 240 of the magnetic light coupler 236 has approximately a 1 mm thick, optically clear UV-cured resin disposed thereon that fully encapsulates the second distal end 274 of the accessory fiber optic cable 166, as discussed below. A pair of crimp rings 231, 233 are disposed about and mechanically crimped against the outer cladding 174 of each of the fiber optic cables 166, 224 and embedded within each of the first and second halves 238, 240 of the magnetic light coupler 236 to prevent separation.

Preferably, both permanent magnets 248, 272 are formed of an axially magnetized neodymium high curie temperature magnet and oriented in complementary pole relationship, so that the S and N poles are disposed in adjacent and abutting relation. Thus, when the solid cylindrical body 266 of the second half 240 of the magnetic light coupler 236 is inserted within the open cylindrical cavity 244 of the first half 238 of the magnetic light coupler 236, the respective exposed second distal end 234 of the supply fiber optic cable 224 is brought into juxtaposed relationship with second distal end 274 of accessory fiber optic cable 166 by the mutual attraction of the permanent magnets 248, 272 in the first and second ends 238, 240 of the magnetic light coupler 236 so as to allow the transmission of light from the light engine 200, through the supply fiber optic cable 224 to the accessory fiber optic cable 166, and ultimately to the dental bite block assembly 10. Preferably, the coupling force is about 1 or 2 pounds force to separate the first and second ends 238, 240 of the magnetic light coupler 236. This provides a relatively secure connection between the first and second halves 238, 240 of the magnetic light coupler 236 to prevent inadvertent separation of the two, while at the same time allows the user to readily separate the magnetic light coupler 236 intentionally when desired. As noted above, preferably the second half 240 of the magnetic light coupler 236 is fully encased within an optically clear UV-cured resin. This is particularly advantageous in that, by so doing, the entire accessory fiber optic cable 166 is adapted for use in an autoclave machine for sterilization of the second fiber optic cable, including the dental accessory 110 at the first distal end 164 of the accessory fiber optic cable 166 and the second half 240 of the magnetic light coupler 236 at the second distal end 274 of the accessory fiber optic cable 166, as has been noted herein. Further, the dentist and/or dental hygienist need carry only the light engine 200 and the supply fiber optic cable 224 attached thereto on their person and to then proceed from patient to patient, without needing to disassemble or sterilize the light engine 200 and supply fiber optic cable 224 attached thereto. Rather, only the accessory fiber optic cable 166, which can be readily disconnected from the supply fiber optic cable 224 as described above, need be sterilized. The fiber optic cables 166, 224 should be sufficiently long so as to provide movement of the dentist and dental hygienist without inadvertently disconnecting the magnetic light coupler 236.

This arrangement for providing a heat engine 200 entirely separate than the dental bite block assembly 10 situated within the patient's mouth has been found to be very advantageous. Particularly in the context of the heat developed with other light sources, such as such as a light source mounted on a headband and disposed on the forehead of the dentist and/or dental hygienist for directing a beam of light into the patient's mouth, the present disclosure offers important advantages in that the heat emitted by the light source on the forehead of the dentist and/or dental hygienist is simply not present. Additionally, the dentist and/or dental hygienist need not worry about carrying around additional batteries to replace batteries that may go dead during use.

A further benefit of the use of polycarbonate materials in conjunction with the light engine is that polycarbonate plastic filters ultraviolet or UV light radiation. The dental profession has recently moved toward the use of UV-cured resins to adhere dental appliances to a patient's mouth. Thus, it is highly desirable that light being provided to a dental patient's mouth not contain UV radiation, and that the dentist and and/or dental hygienist be provided with the highest level of control over the application of UV radiation to a dental patient.

In a further feature of the present disclosure, an inspection filament 280 can be provided. Such an inspection filament 280, preferably comprising a 0.5 mm fiber optic cable also fabricated from PMMA, is free at a first distal end 282 for insertion into a patient's mouth. The first distal end 282 is completely exposed to allow full transmission of light from the light engine 200 through the supply fiber optic cable 224 and the inspection filament 280 to provide intense light within the patient's mouth. Because the inspection filament 280 is highly flexible, it can be manipulated by the dentist and/or dental hygienist to illuminate and allow inspection literally anywhere within the patient's mouth. Thus, the dentist and/or dental hygienist can look behind the patient's teeth and obtain a visual inspection of the enamel and structures of the patient's teeth.

A second distal end 284 of the inspection filament 280 can be heated, preferably on a ceramic heating device, to slightly melt the second distal end 284 of the inspection filament 280 to form a cone-shaped shoulder 286. It is been found that the use of a smooth ceramic-coated heating device, heated to 200° C.-230° C., provides a mirror-like polished surface finish to the exposed surface 288 of the cone-shaped shoulder 286 on the second distal end 284 of the inspection filament 280, which allows effective light transmission without any loss of intensity through the inspection filament 280.

An inspection filament coupler 290 is constructed similar to that of the second half 240 of the magnetic light coupler 236, and generally comprises a solid cylindrical body 292. However, the inspection filament coupler 290 is provided with stainless steel guide 298, such as a stainless steel hypodermic needle, having a through hole 294 with an inner diameter slightly larger than the outer diameter of the inspection filament 280, but slightly smaller than the outer diameter of the cone-shaped shoulder 286.

In use, the first distal end 282 of the inspection filament 280 is inserted through the through hole 294 proximate the magnet end 272 of the inspection filament coupler 290 and pulled through the through hole 294 until the cone-shaped shoulder 286 on the second distal end 284 of the inspection filament 280 abuts a base 296 of the inspection filament coupler 290 and prevents further motion. The solid cylindrical body 292 of the inspection filament coupler 290, which has an outer diameter slightly less than the inner diameter of the open cylindrical cavity 244 of the first half 238 of the magnetic light coupler 236, is then inserted into the open cylindrical cavity 244, as described above. With the inspection filament 280 thus connected with the light engine 200, light is caused to pass through the supply fiber optic cable 224, inspection filament coupler 290, and the inspection filament 280 to the patient's mouth for use in visual inspection of the patient's teeth. It believed that the intensity of the illumination offered by the inspection filament 280 disclosed herein can allow detection of bubbles and cavities interior to the structure of the tooth, which can be particularly advantageous in the dental arts.

A particularly advantageous feature of the inspection filament 280 disclosed herein is that the inspection filament 280 can be inexpensively and easily produced. Thus, the inspection filament 280 disclosed herein is adaptable for a single use, eliminating the need for it to be sterilized for subsequent patients. That is, a dentist and/or dental assistant can simply use a new inspection filament 280 for each patient as the need may arise, without concern for cross-contamination. Only the inspection filament coupler 290 need be autoclaved. However, since the inspection filament coupler 290 is otherwise fully encapsulated within polycarbonate plastic, it can be readily and repeatedly autoclaved without degrading its performance.

The axially magnetized, planar single-mode fiber optic linear coupling system disclosed above may accordingly be used in an optical fiber lighting system for transmitting light to at least one accessory fiber optic cables 116 fibers from one supply fiber optic cable 224. The coupling system is configured so that the magnetic flux is transferred about the flat end of the ring faces of the magnetic assembly, allowing quick and easy assembly and disassembly with one hand of the operator, while allowing quick and easy changing of accessory dental instruments. The two permanent magnets 248, 272, which form two axially magnetized ring magnets embedded into separate tubes, with a single-mode optical fiber 166, 224 running through the center to connect and disconnect accessory medical instruments to a light source.

The axially magnetized, linear type single-mode fiber optic magnetic coupling system also enables convenient sterilization of accessory medical devices. The optical fiber coupling system further allows for the use of a cost effective disposable inspection filament 280 as a fiber optic light guide.

It will be understood by one having ordinary skill in the art that construction of the described invention and other components is not limited to any specific material. Other exemplary embodiments of the invention disclosed herein may be formed from a wide variety of materials, unless described otherwise herein.

For purposes of this disclosure, the term "coupled" (in all of its forms, couple, coupling, coupled, etc.) generally means the joining of two components (electrical or mechanical) directly or indirectly to one another. Such joining may be stationary in nature or movable in nature. Such joining may be achieved with the two components (electrical or mechanical) and any additional intermediate members being integrally formed as a single unitary body with one another or with the two components. Such joining may be permanent in nature or may be removable or releasable in nature unless otherwise stated.

For purposes of this disclosure, the term "operably connected" generally means that one component functions with respect to another component, even if there are other components located between the first and second component, and the term "operable" defines a functional relationship between components.

It is also important to note that the construction and arrangement of the elements of the invention as shown in the exemplary embodiments is illustrative only. Although only a few embodiments of the present innovations have been described in detail in this disclosure, those skilled in the art who review this disclosure will readily appreciate that, unless otherwise described, many modifications are possible (e.g., variations in sizes, dimensions, structures, shapes and proportions of the various elements, values of parameters, mounting arrangements, use of materials, colors, orientations, etc.) without materially departing from the novel teachings and advantages of the subject matter recited. For example, elements shown as integrally formed may be constructed of multiple parts or elements shown as multiple parts may be integrally formed, the operation of the interfaces may be reversed or otherwise varied, the length or width of the structures and/or members or connector or other elements of the system may be varied, the nature or number of adjustment positions provided between the elements may be varied. It should be noted that the elements and/or assemblies of the system may be constructed from any of a wide variety of materials that provide sufficient strength or durability, in any of a wide variety of colors, textures, and combinations. Accordingly, all such modifications are intended to be included within the scope of the present innovations. Other substitutions, modifications, changes, and omissions may be made in the design, operating positions, and arrangement of the desired and other exemplary embodiments without departing from the spirit of the present innovations.

It will be understood that any described processes or steps within described processes may be combined with other disclosed processes or steps to form structures within the scope of the present invention. The exemplary structures and processes disclosed herein are for illustrative purposes and are not to be construed as limiting.

It is also to be understood that variations and modifications can be made on the aforementioned structures and methods without departing from the concepts of the present invention, and further it is to be understood that such concepts are intended to be covered by the following claims unless these claims by their language expressly state otherwise.

What is claimed is:

1. A dental bite block assembly comprising:
   a U-shaped mounting base having an upper bite portion, a lower bite portion, a central portion, an accessory mount, a first magnetically energetic material embedded in the central portion of the U-shaped mounting base proximate the accessory mount, and a circular recess concentrically disposed proximate the first magnetically energetic material; and
   a dental accessory fabricated of a stainless steel metal wire fabricated of a second magnetically energetic material that defines a dental bite block mount detachably coupled with the accessory mount of the U-shaped mounting base, wherein with the dental bite block mount coupled with the accessory mount, the first magnetically energetic material embedded in the central portion of the U-shaped mounting base and the second magnetically energetic material are in operable magnetic engagement with each other to retain the dental bit block mount within the accessory mount.

2. The dental bite block assembly of claim 1, wherein the dental accessory further comprises a first distal end having a curved portion for receiving a dental tool and a second distal end having a curved portion that forms the dental bite block mount and which is received within the circular recess of the central portion of the U-shaped mounting base.

3. A dental bite block assembly comprising:
   a U-shaped mounting base having an upper bite portion, a lower bite portion, a central portion, an accessory mount disposed on the central portion of the U-shaped mounting base and comprises a forwardly facing recess, and a first magnetically energetic material embedded in the central portion of the U-shaped mounting base proximate the accessory mount, wherein the U-shaped mounting base comprises an inner bite block member having a substantially U-shaped configuration and having an upper bite portion, a lower bite portion, and a central portion having an external surface whereon the accessory mount is disposed, and an outer bite block member having a substantially U-shaped configuration and having an upper bite portion disposed in juxtaposed relation with the upper bite portion of the inner block member, a lower bite portion disposed in juxtaposed relation with the lower bite portion of the inner block member, and a central portion in juxtaposed relation with the central portion of the inner block member, the central portions of inner bite block member and the outer bite block member cooperating to form a cavity proximate the accessory mount within which the first magnetically energetic material is received, and wherein the central portion of the inner block member has a rearward facing surface and the central portion of the outer block member has a forward facing surface, and the cavity comprises a circular recess formed on one of either the rearward facing surface of the inner block member or the forward facing surface of the outer block member, whereby the first magnetically energetic material is received and sealingly encased within the cavity within the U-shaped mounting base.

4. The dental bite block assembly of claim 3, wherein a recess in the central portion of the U-shaped mounting base is a semicircular recess having an open lower portion thereof concentrically disposed proximate the first magnetically energetic material embedded in the central portion of the U-shaped mounting base and the rearwardly facing member of the dental bite block mount within which the second magnetically energetic material is disposed comprises a semicircular projection that is fittingly received within the semicircular recess of the central portion of the U-shaped mounting base, and wherein the lower bite portion of the U-shaped mounting base comprises a pair of channels extending forwardly on each lateral side of the lower bite portion of the U-shaped mounting base proximate the open lower portion of the semicircular recess within which a locking tab proximate each lateral side of the rearwardly facing member of the dental bite block mount is slidingly received.

* * * * *